(12) United States Patent
Crameri et al.

(10) Patent No.: US 6,605,723 B2
(45) Date of Patent: Aug. 12, 2003

(54) PROCESS FOR THE PREPARATION OF ETHANESUL FONYL-PIPERIDINE DERIVATIVES

(75) Inventors: Yvo Crameri, Oberwil (CH); Michelangelo Scalone, Birsfelden (CH); Pius Waldmeier, Wegenstetten (CH); Ulrich Widmer, Rheinfelden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 47 days.

(21) Appl. No.: 09/809,691

(22) Filed: Mar. 15, 2001

(65) Prior Publication Data

US 2001/0037026 A1 Nov. 1, 2001

(30) Foreign Application Priority Data

Mar. 22, 2000 (EP) .............................. 00106210

(51) Int. Cl.[7] ..................... C07D 211/06; C07D 211/40
(52) U.S. Cl. .................. 546/216; 546/219; 546/236
(58) Field of Search ................... 546/216, 219, 546/236

(56) References Cited

U.S. PATENT DOCUMENTS 6,310,213 B1 * 10/2001 Alanine et al. ............. 546/216

FOREIGN PATENT DOCUMENTS

| EP | 0 718 265 | 6/1996 |
| EP | 0 901 997 | 3/1999 |
| WO | 95/25721 | 9/1995 |
| WO | WO 00/75109 | 12/2000 |

OTHER PUBLICATIONS

S.M. McElvain, *Piperidine Derivatives. XX. The Preparation and Reactions of 1–Methyl–3–piperidine*, J. Am. Chem. Soc., vol. 71, pp. 896–900 (1949).
Helv. Chimica Ata., (1954) 20, p. 178.
J. Chem. Soc. Perkin. Trans. 1, (1998) 3673.

* cited by examiner

Primary Examiner—Alan L. Rotman
Assistant Examiner—Raymond Covington
(74) Attorney, Agent, or Firm—George W. Johnston; Patricia S. Rocha-Tramaloni; Kimberly J. Prior

(57) ABSTRACT

The present invention relates to a new process for the preparation of compounds of the formulae

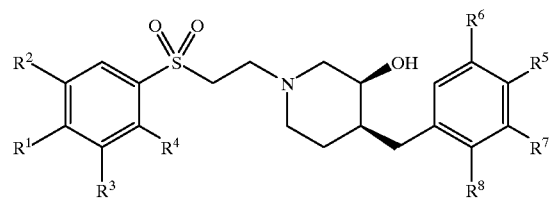

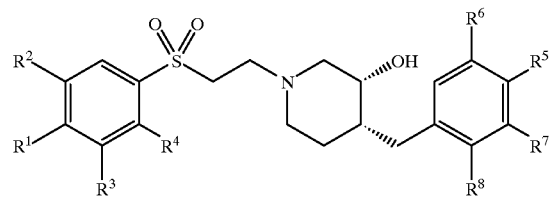

and their pharmaceutically acceptable acid addition salts, which are NMDA (N-methyl-D-aspartate)-receptor-subtype selective blockers.

16 Claims, No Drawings

PROCESS FOR THE PREPARATION OF ETHANESULFONYL-PIPERIDINE DERIVATIVES

BACKGROUND OF THE INVENTION

The present invention relates to a process for the preparation of the compounds of the formulae

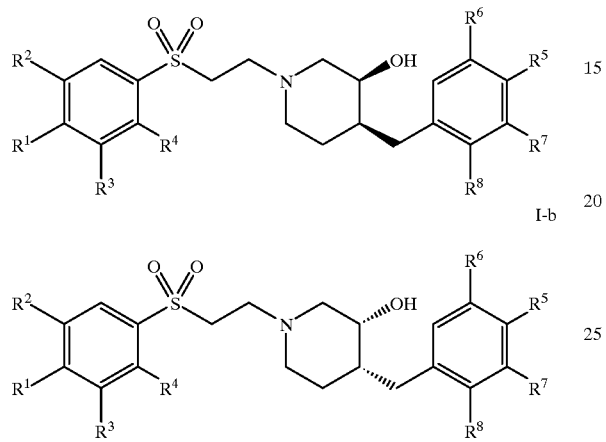

where $R^1$–$R^4$ are, independently from each other, hydrogen, halogen, hydroxy, amino, nitro, lower-alkyl-sulfonylamido, or acetamido; $R^5$–$R^8$ are, independently from each other hydrogen, lower-alkyl, halogen, trifluoromethyl or lower-alkoxy; and their pharmaceutically acceptable acid addition salts, especially the compounds formula I-a. These compounds are active as NMDA (N-methyl-D-aspartate) receptor-subtype selective blockers.

Under pathological conditions of acute and chronic forms of neurodegeneration overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors displaying different pharmacological properties. Possible therapeutic indications for NMDA receptor subtype specific blockers such as the compounds of formula I include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, diseases such as schizophrenia, anxiety and depression and acute/chronic pain. Ethanesulfonyl-piperidine derivatives that are NMDA (N-methyl-D-aspartate)-receptor-subtype selective blockers also have a key function in modulating neuronal activity and plasticity and are key players in mediating processes underlying development of CNS including learning and memory formation and function.

The compounds of formula I and their pharmaceutically acceptable salts can be prepared by methods known in the art, e.g. in WO 95/25721, for example by processes described below, which comprises a) reacting a compound of formula

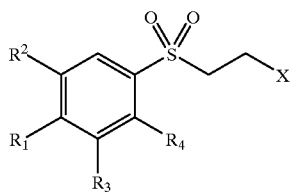

with a compound of formula

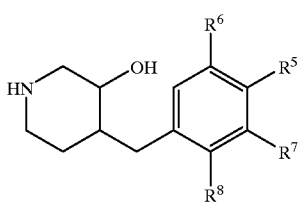

to a compound of formula

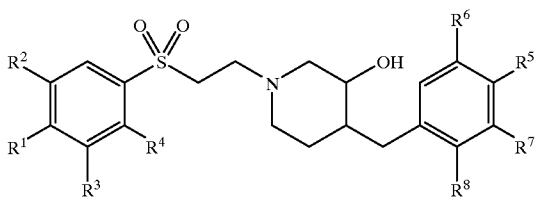

wherein the substituents are as defined above and X signifies a leaving group, and, if desired, b) converting the compound of formula I obtained into a pharmaceutically acceptable acid addition salt, and, if desired, c) converting a racemic mixture at the stage of formula III or at the stage of formula I into enantiomeric compounds III-a, III-b

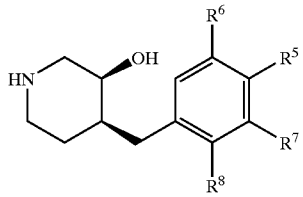

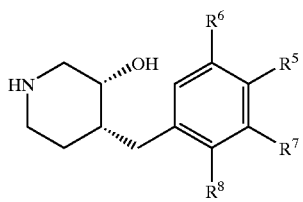

or I-a, I-b respectively, thus obtaining optically pure compounds. However, the above processes usually lead to yields of 10% or less of the desired compound due to the poor efficiency of the methods employed, i.e. resolution by crystallization of diasteromeric salts.

SUMMARY OF THE INVENTION

It has now been found that the compounds of formula I-a and I-b can be prepared more effectively and with considerably higher yield if manufactured according to reaction scheme 1.

All starting materials are known compounds or may be prepared by methods known in the art.

wherein
R$^1$–R$^8$ are as defined above;
R$^9$ is an amino protecting group, preferably benzyl;
R$^{10}$ and R$^{10'}$ are independently a carboxylic acid protecting group;
Y and X represent independently a leaving group; and
AZ signifies a mineral acid from the group of HBF$_4$, H$_2$SO$_4$, HPF$_6$, HBr, HI, HCl, HSbF$_6$ or HClO$_4$, or a strong organic acid from the group of C$_{1-8}$-alkylSO$_3$H, picric acid, formic acid, a lower alkylcarboxylic acid

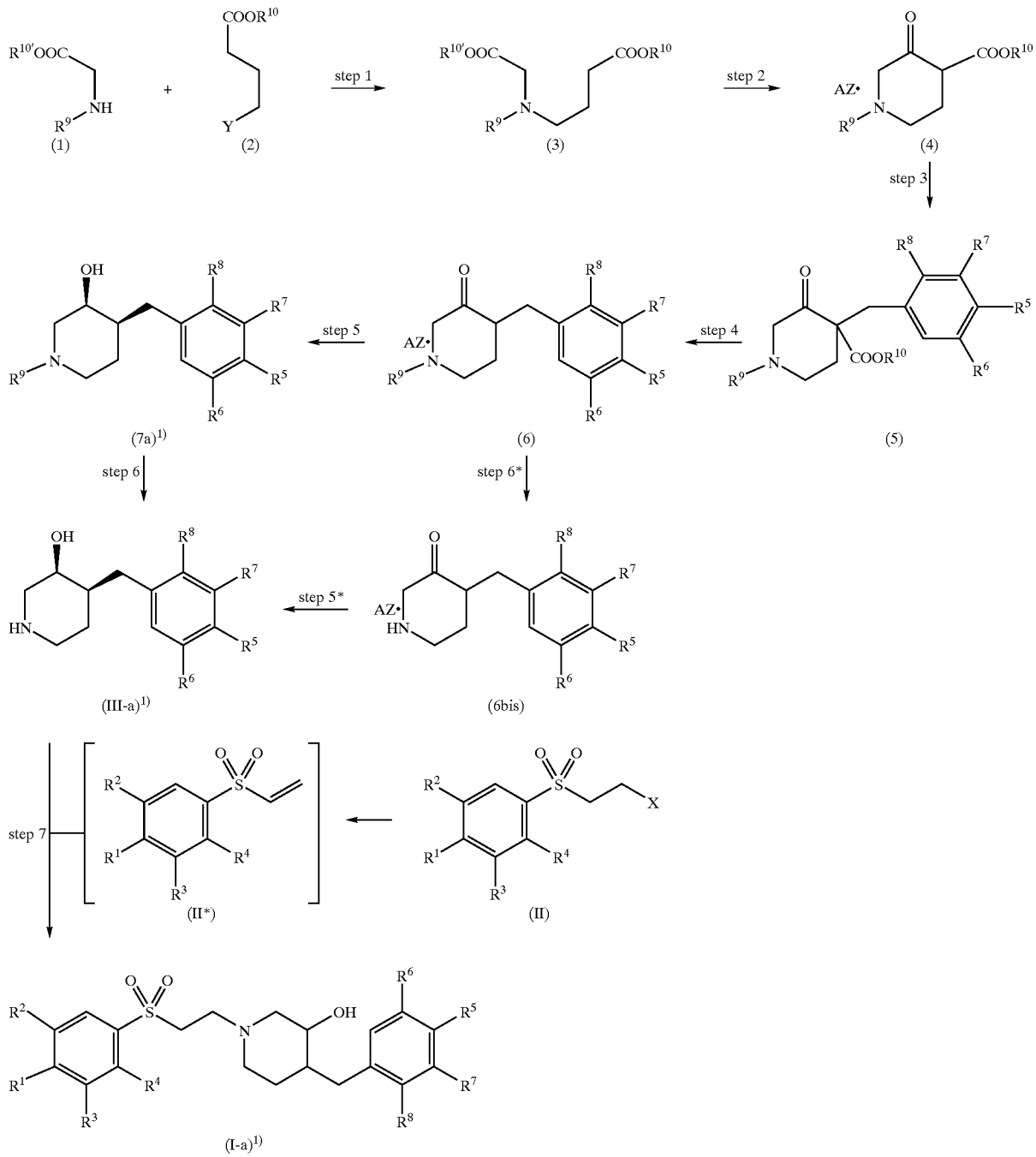

1) or the corresponding cis configured enantiomer, 7b, III-b and I-b, respectively such as e.g. acetic acid, propionic acid or trifluoroacetic acid, or a dicarboxylic acid, such as e.g. oxalic acid, succinic acid, maleic acid, tartaric acid or phthalic acid.

Step 5 (asymmetric hydrogenation) and step 6 (deprotection of the ring nitrogen) can be inverted (Step 6* and step 5*).

Accordingly, this invention is directed to a process (Process A) for the preparation of compounds of formulae

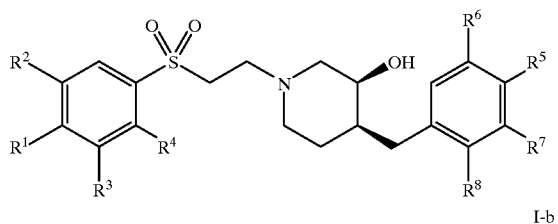

wherein $R^1$–$R^4$ are, independently from each other, hydrogen, halogen, hydroxy, amino, nitro, lower-alkyl-sulfonylamido, or acetamido; $R^5$–$R^8$ are, independently from each, other hydrogen, lower-alkyl, halogen, trifluoromethyl or lower-alkoxy; and their pharmaceutically acceptable acid addition salts; which process comprises a) reacting a protected amino acid ester (1)

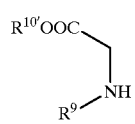

with a 4-substituted butyric acid derivative (2)

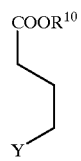

wherein $R^9$ is an amino protecting group, preferably benzyl; $R^{10}$ and $R^{10'}$ are independently a carboxylic acid protecting group; and Y represents a leaving group; in the presence of a base to obtain the protected alkoxycarbonylmethyl amino butyric acid derivative (3);

b) cyclising the protected alkoxycarbonylmethyl amino butyric acid derivative (3)

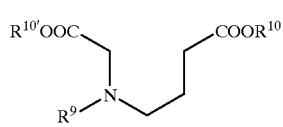

wherein the symbols are as defined above to obtain the protected alkyl 3-oxo-piperidine carboxylate salt(4);

c) benzylating the protected alkyl 3-oxo-piperidine carboxylate salt (4)

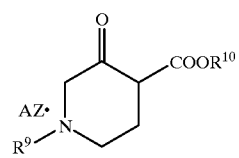

wherein AZ signifies a mineral acid or a strong organic acid to obtain the benzylated protected alkyl 3-oxo-piperidine carboxylate (5);

d) decarboxylating the benzylated protected alkyl 3-oxo-piperidine carboxylate (5)

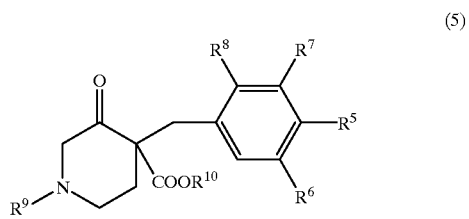

wherein the symbols are as defined above; in presence of a strong acid to obtain the salt of formula (6);

e) asymmetrically hydrogenating the salt of formula (6)

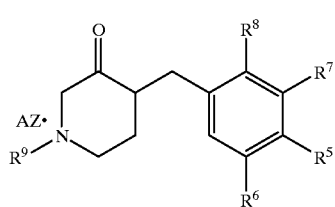

wherein $R^9$ is an amino protecting group; in presence of a ruthenium complex with a chiral diphosphine ligand and a chiral diamine, wherein the diphosphine has an (S) configuration and the diamine has an (R,R) configuration or the diphosphine has an (R) configuration and the diamine has an (S,S) configuration, and an organic or inorganic base, to obtain the compound of formula (7a) or (7b); and deprotecting the compound of formula (7a) or (7b)

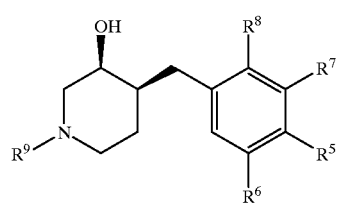

(7b)

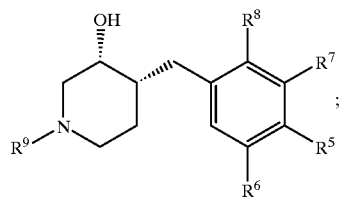

wherein the symbols are as defined above; or
asymmetrically hydrogenating the salt of formula (6bis)

(6bis)

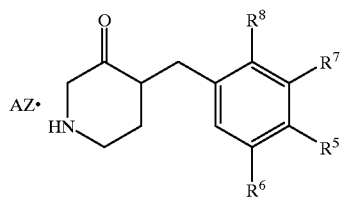

in presence of a ruthenium complex with a chiral diphosphine ligand and a chiral diamine, wherein the diphosphine has an (S) configuration and the diamine has an (R,R) configuration or the diphosphine has an (R) configuration and the diamine has an (S,S) configuration, and a organic or an inorganic base, to obtain the piperidine derivative of formula III-a or III-b; and f) reacting the piperidine derivative of formula III-a or III-b III-a

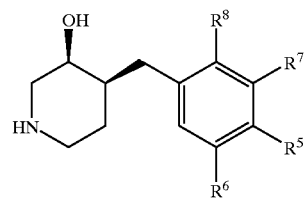

III-b

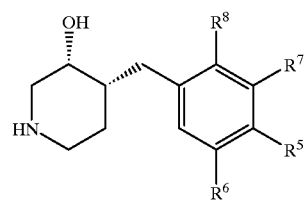

wherein the symbols are as defined above; with the reactive vinyl sulfone intermediate

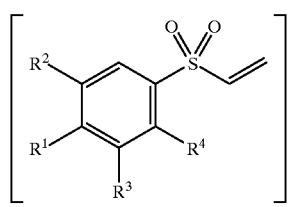

which is obtained by treating the sulfone derivative of formula II

II

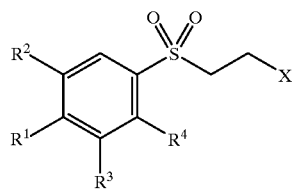

wherein $R^1$–$R^4$ are as defined above; and X is a leaving group; with a base; in the presence of a base to form the desired compound of formula I-a or I-b.

The above process provides compounds of formulae I-a and I-b, which are the cis compounds of the compound of formula I. By this process, trans compounds of formula I are excluded.

The above process is particularly preferred for the preparation of compounds of formula I-a. In this preferred process, the ruthenium complex of step e), the diphosphine has an (S) configuration and the diamine has an (R,R) configuration.

This invention is also directed to Process B, which is the above process for the preparation of compounds of formulae

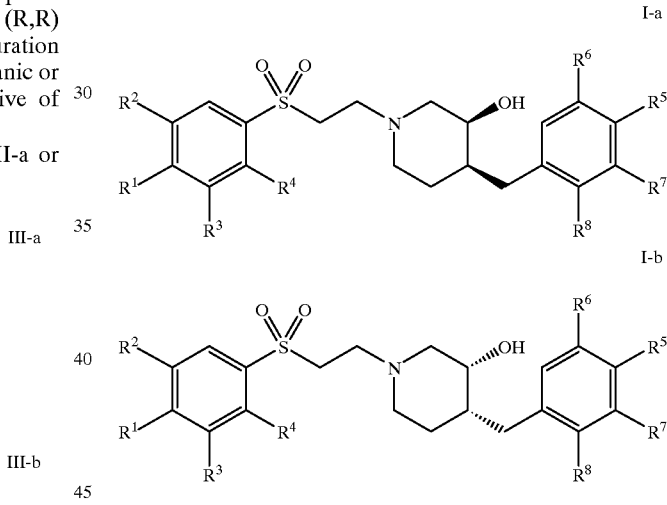

wherein $R^1$–$R^4$ are, independently from each other, hydrogen, halogen, hydroxy, amino, nitro, lower-alkyl-sulfonylamido, or acetamido; $R^5$–$R^8$ are, independently from each, other hydrogen, lower-alkyl, halogen, trifluoromethyl or lower-alkoxy; and their pharmaceutically acceptable acid addition salts; which process comprises a) deprotonating a substituted thiophenol derivative of formula (8)

(8)

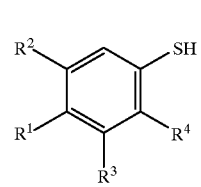

wherein the symbols are as defined above; in presence of a strong inorganic or organic base and subsequently reacting it with 2-haloethanol to obtain the thioether of formula (9);

b) oxidizing the thioether of formula (9)

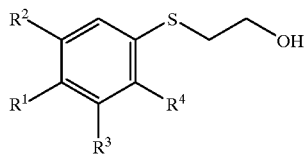
(9)

wherein the symbols are as defined above; in presence of an oxidative agent to obtain the sulfone derivative of formula (10);

c) replacing the hydroxy group of the sulfone derivative of formula (10)

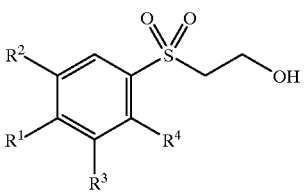
(10)

wherein the symbols are as defined above; by a halogen atom in the presence of pyridine in dichloromethane to obtain the sulfone derivative of formula II; and d) treating the sulfone derivative of formula II

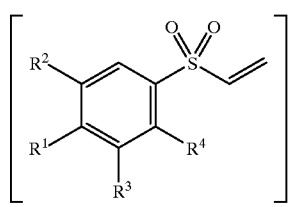
II wherein $R^1$–$R^4$ are as defined above; and X is halogen; with a base to form the corresponding reactive vinyl sulfone intermediate of formula II*

II*

$$\left[ \text{structure} \right]$$

which is then reacted with the piperidine derivative of formula

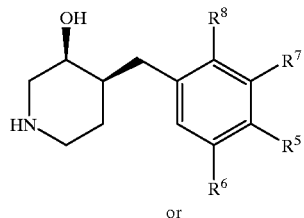
III-a or

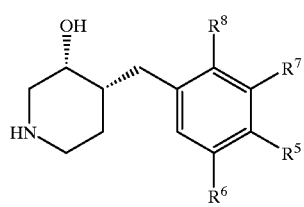
III-b wherein the symbols are as defined above in presence of a base to obtain the compounds of formulae I-a or I-b.

This invention is also directed to compounds of formula (6) and (6 bis)

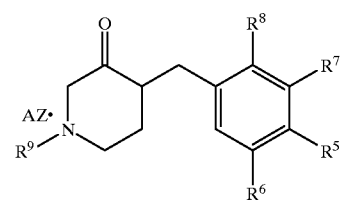
(6)

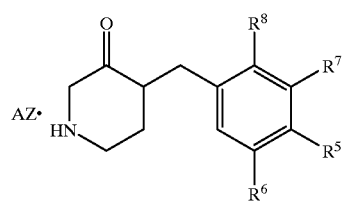
(6bis)

wherein $R^1$–$R^4$ are, independently from each other, hydrogen, halogen, hydroxy, amino, nitro, lower-alkyl-sulfonylamido, or acetamido; $R^5$–$R^8$ are, independently from each, other hydrogen, lower-alkyl, halogen, trifluoromethyl or lower-alkoxy and their pharmaceutically acceptable acid addition salts.

DETAILED DESCRIPTION OF THE INVENTION

In more detail, this invention is also directed to processes which are part of Process A or Process B, for instance Process C, a process for the preparation of compounds of formula

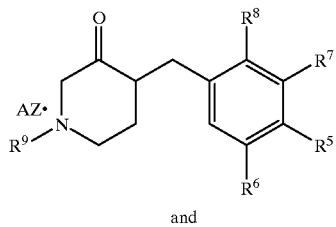

(6)

and

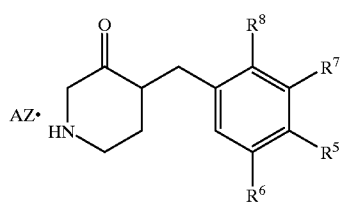

(6bis)

wherein $R^1$–$R^4$ are, independently from each other, hydrogen, halogen, hydroxy, amino, nitro, lower-alkyl-sulfonylamido, or acetamido; $R^5$–$R^8$ are, independently from each other, hydrogen, lower-alkyl, halogen, trifluoromethyl or lower-alkoxy; $R^9$ is an amino protecting group; AZ signifies a mineral acid or a strong organic acid; which process comprises a) reacting a protected amino acid ester (1)

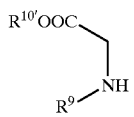

(1)

with a 4-substituted butyric acid derivative (2)

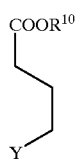

(2)

wherein
  $R^9$ is an amino protecting group, preferably benzyl;
  $R^{10}$ and $R^{10'}$ are independently a carboxylic acid protecting group; and Y represents a leaving group; in the presence of a base; to obtain the protected alkoxycarbonylmethylamino butyric acid derivative (3);
b) cyclising the protected alkoxycarbonylmethyl amino butyric acid derivative (3)

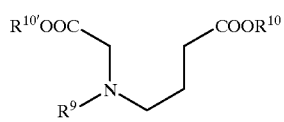

(3)

wherein the symbols are as defined above to obtain the protected alkyl-3-oxo-piperidine caboxylate salt (4);

c) benzylating the protected alkyl 3-oxo-piperidine carboxylate salt(4)

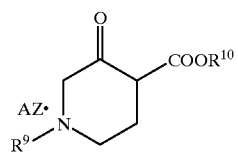

(4)

wherein AZ signifies a mineral acid or a strong organic acid to obtain the benzylatedprotected alkyl-3-oxo-piperidine carboxylate (5);

d) decarboxylating the benzylated protected alkyl 3-oxo-piperidine carboxylate (5)

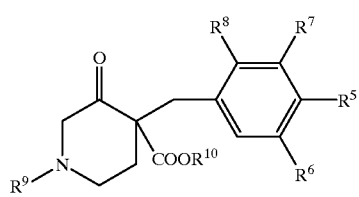

(5)

wherein the symbols are as defined above; in presence of a strong acid to obtain the compound of formula (6); and, to obtain the compound of formula (6bis), deprotecting compound of formula (6).

This invention is also directed to Process D, a process for the preparation of compounds of formula

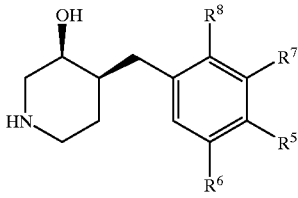

III-a and

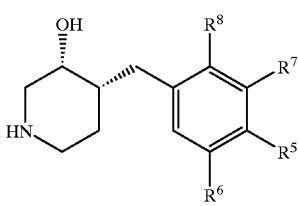

III-b wherein $R^1$–$R^4$ are, independently from each other, hydrogen, halogen, hydroxy, amino, nitro, lower-alkyl-sulfonylamido, or acetamido; $R^5$–$R^8$ are, independently from each, other hydrogen, lower-alkyl, halogen, trifluoromethyl or lower-alkoxy; and their pharmaceutically acceptable acid addition salts, which process comprises asymmetrically hydrogenating a salt of formula (6)

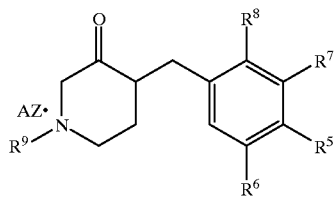

(6)

wherein $R^9$ is an amino protecting group; in presence of a ruthenium complex with a chiral diphosphine ligand and a chiral diamine wherein the diphosphine has an (S) configuration and the diamine has an (R,R) configuration or the diphosphine has an (R) configuration and the diamine has an (S,S) configuration and an organic or inorganic base to obtain the compound of formula (7a) or (7b);
and deprotecting the compound of formula (7a) or (7b)

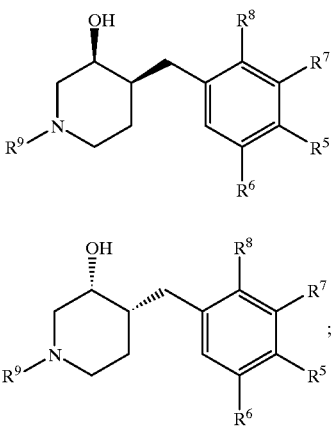

(7a)

(7b)

wherein the symbols are as defined above; or
deprotecting the compound of formula (6); and asymmetrically hydrogenating the salt of formula (6bis)

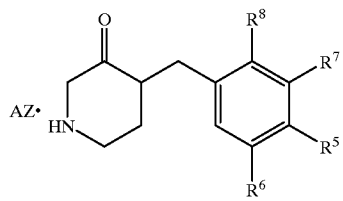

(6bis)

in presence of a ruthenium complex with a chiral diphosphine ligand and a chiral diamine wherein the diphosphine has an (S) configuration and the diamine has an (R,R) configuration or the diphosphine has an (R) configuration and the diamine has an (S,S) configuration and an organic or inorganic base to obtain the piperidine derivative of formula III-a or III-b;

In any relevant process of this invention where asymmetric hydrogenation occurs, for example Process A or D, it is possible to direct this process to the preparation of compounds of formula III-a by using a ruthenium complex where the diphosphine has an (S) configuration and the diamine has an (R,R) configuration.

Similarly, in any relevant process of this invention, for example Process A, and especially D, the ruthenium complex used for the asymmetric hydrogenation is preferably a complex of formula IV

wherein E is a halogen atom; L is a chiral diphosphine ligand; and A is a chiral diamine.

In this complex, the chiral diphosphine ligands are ligands of formulae

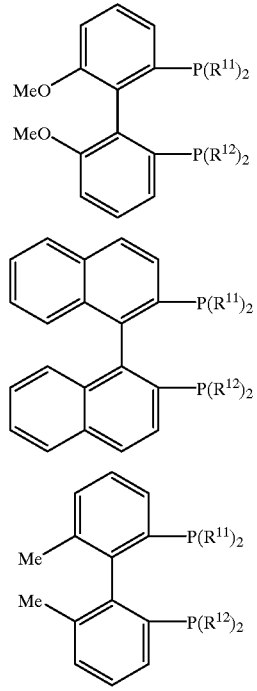

and $R^{11}$ and $R^{12}$ are independently from each other alkyl, cycloalkyl, optionally substituted phenyl or a heterocyclic ring, and the chiral diamines are compounds of formulae

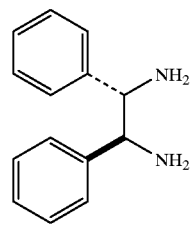

V

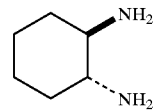

VI

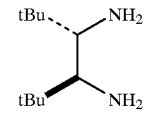

VII

-continued

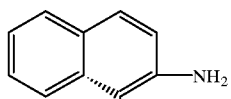
VIIII

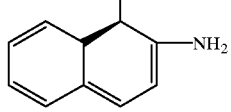
IX

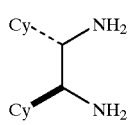
X

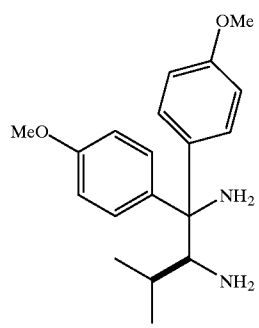

wherein tBu signifies tert.-butyl, Me is methyl and Cy stands for cyclohexane.

In any relevant process of this invention, for example Process A, D, and the process immediately above, preferably $R^{11}$ and $R^{12}$ are independently from each other

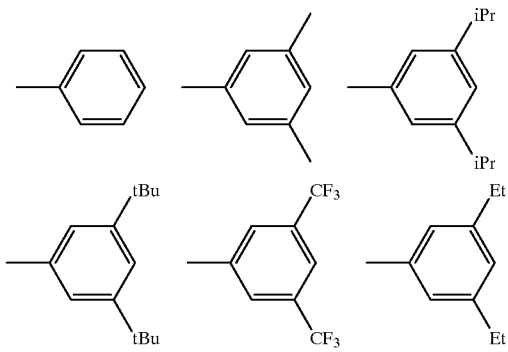

where iPr is iso-propyl and tBu is tert.-butyl. Also, it is preferred that the chiral diamine is a compound of formula V.

In any relevant process of this invention, for example Process A or D, and especially the processes of the above two paragraphs, the amount of chiral diamine used in the reaction is preferably from about 0.5 to about 2.5 equivalents based on the Ru-complex Similarly, the organic or inorganic base is preferably present in the amount of about 1.0 to about 0.001 mol equivalents, and more preferably 0.05–0.2 mol equivalents, with respect to the substrate in addition to the about 1 mol equivalent of organic or inorganic base present for the neutralization of the acid salt of the substrate (6) or (6 bis). Preferably both these conditions exist in any of these processes.

A preferred organic or inorganic base for any of the above-described processes is potassium tert.-butylate.

This invention is also directed to a process of Process B above, for the preparation of compounds of formula

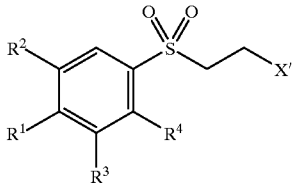
II wherein $R^1$–$R^4$ are, independently from each other, hydrogen, halogen, hydroxy, amino, nitro, lower-alkyl-sulfonylamido, or acetamido; and X' is halogen; which process comprises a) deprotonating a substituted thiophenol derivative of formula (8)

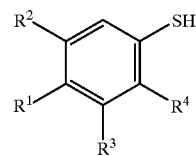
(8)

wherein the symbols are as defined above, in presence of a strong inorganic or organic base and subsequently reacting it with 2-haloethanol to obtain the thioether of formula (9);

b) oxidizing the thioether of formula (9)

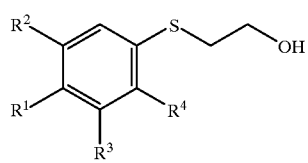
(9)

wherein the symbols are as defined above; in presence of an oxidative agent to obtain the sulfone derivative of formula (10);

c) replacing the hydroxy group of the sulfone derivative of formula (10)

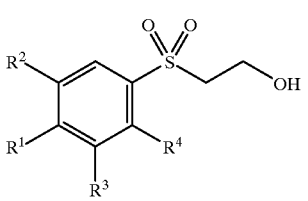
(10)

wherein the symbols are as defined above, by a halogen atom in the presence of pyridine in dichloromethane to obtain the compound of formula II.

The processes of this invention involve several key steps such as new methods for the preparation of the intermediates of formula II

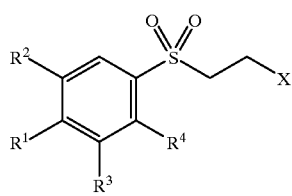

II and of formula III, especially by a new approach for the enantioselective preparation of the intermediate of formula III, i.e. of the intermediates of formulae

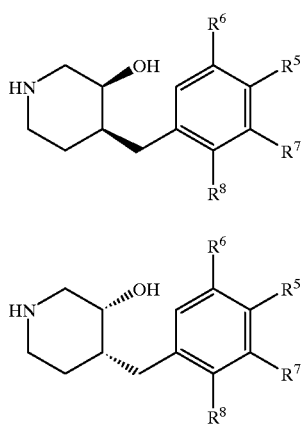

wherein the symbols are as defined above.

The processes of this invention for the preparation of the intermediate III-a and III-b involve two key reactions:

a) A process of this invention for the preparation of the compound of formula (4) or of a salt thereof starting with a protected glycine (1) and a butyric acid derivative (2). The process of this inventions considerably shorter and gives much higher yields than the conventionally used processes described in Helv. Chim. Acta, 1954, 20, 178; J. Am. Chem. Soc., 1948, 71, 896 or in J. Chem. Soc. Perkin Trans. 1, 1998, 3673.

Scheme 2

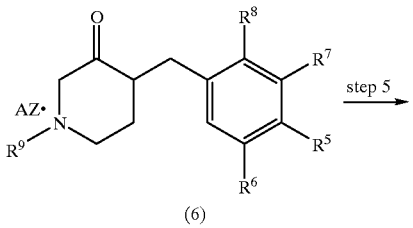

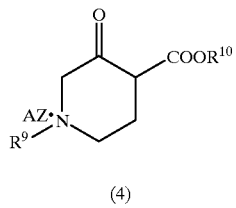

wherein
Y signifies a leaving group;
$R^{10}$ and $R^{10'}$ signify independently a carboxylic acid protecting group;
$R^9$ signifies an amino protecting group, preferably benzyl; and
AZ is as defined above.

The compound of formula (4) is then transformed according to standard procedures as depicted in reaction scheme 1, by benzylation in position 4 of the piperidine ring to form a compound of formula (5) (step 3). Subsequent decarboxylation and formation of the stable salt yields a compound of formula (6) (step 4).

b) Both the free base of formula (6 and 6bis) and its salts can be submitted to the asymmetric hydrogenation reaction, which proceeds with concomitant dynamic-kinetic resolution. However, due to the limited stability of the free base, according to the invention a salt thereof is preferentially submitted to the asymmetric hydrogenation reaction in the presence of a homogeneous chiral catalyst (i.e. and (S,S) or (R,R) catalyst), a chiral diamine and an organic or an inorganic base (step 5 and step 5*, respectively).

Scheme 3

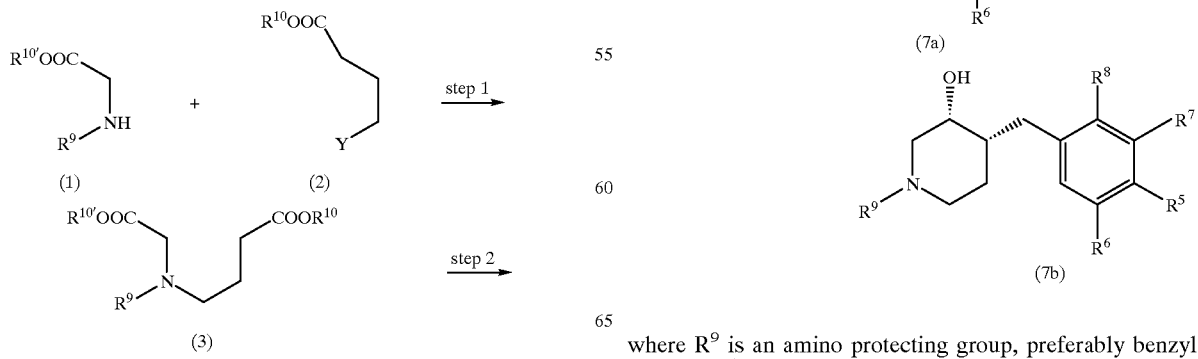

where $R^9$ is an amino protecting group, preferably benzyl, AZ and $R^5$–$R^8$ are as defined above.

The amino protecting group $R^9$ may be removed in step 6* before submitting the unprotected compound of formula (6bis) to the asymmetric hydrogenation (step 5*):

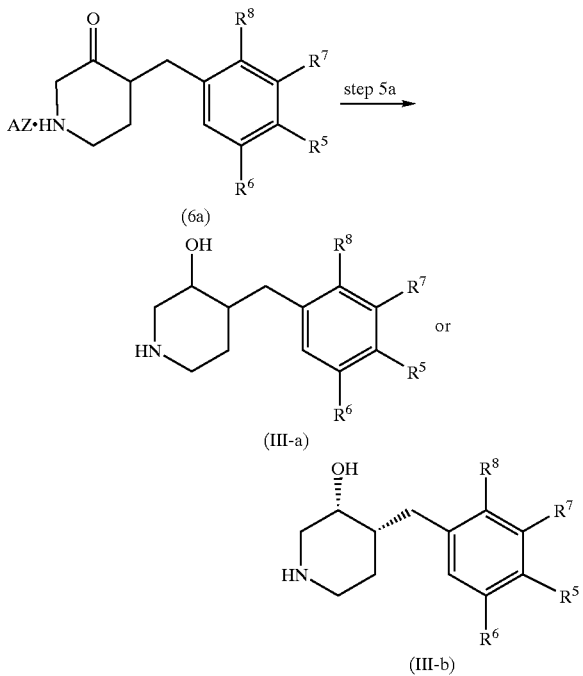

wherein AZ and $R^5$–$R^8$ are as defined above.

Furthermore, the invention relates to a process for the preparation of intermediates of formula (II) which are conventionally prepared starting from substituted thiophenol (8) and 2-bromoethanol and subsequent transformation with $SOCl_2$ to obtain the highly mutagenic and unstable substituted (2-chloroethylsulfanyl)-benzene. The new and enhanced process for the preparation of intermediates of formula (II) avoids the presence of said highly mutagenic and unstable compound:

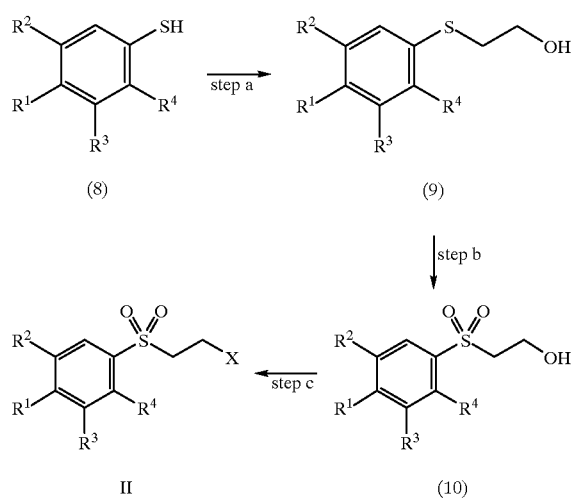

wherein X is a leaving group, preferably a halogen, and $R^1$–$R^4$ are as defined above.

The invention is thus concerned with processes for the preparation of chiral compounds of formula I-a and I-b, respectively, which comprise:

Step 1, reacting a protected amino acid ester (1) with a 4-substituted butyric acid derivative (2) in the presence of a base to form an N-protected alkyloxycarbonylmethyl-amino-butyric acid derivative (3); preferred bases for the present reaction are organic bases such as triethylamine, ethyl-diisopropylamine, or inorganic bases such as $K_2CO_3$ or $Na_2CO_3$. The reaction is carried out in an inert polar solvent preferably in dimethylformamide (DMF), dioxane or acetonitrile. The reaction is carried out at a temperature between 0° C. and 120° C., preferably at a temperature between 40° C. and 80° C.

Step 2, cyclising the protected alkoxycarbonylmethyl amino butyric acid derivative (3) in a Dieckmann condensation to yield protected alkyl 3-oxo-piperidine carboxylate (4) which is isolated as a salt from a mineral acid or a strong organic acid, preferably as the hydrochloride salt. The reaction is preferably carried out in an apolar aromatic solvent such as toluene at a temperature of about 40° C. to about 120° C., preferably at a temperature of about 85° C.

Step 3, benzylating the protected alkyl 3-oxo-piperidine carboxylate (4) salt. This reaction is well known in the art and can be carried out for example in the presence of a base and an appropriate solvent, such as for example with potassium-tert.-butoxyde in tetrahydrofuran (THF), with NaH in THF, $NaOC_2H_5$ in ethanol, $K_2CO_3$ in THF or in dimethylformamide (DMF).

Step 4, decarboxylation of the benzylated N-protected alkyl 3-oxo-piperidine carboxylate (5). The decarboxylation reaction is carried out by methods known in the art, for example by heating in the presence of a strong acid such hydrochloric acid, sulfuric acid and the like. The resulting salt is identified by formula (6) or (6bis).

Step 5 and 5*, asymmetric hydrogenation of the salt of formula (6) or (6bis) in presence of a ruthenium complex with a chiral diphosphine ligand, a chiral diamine and an organic or an inorganic base.

Typical of Steps 5 and 5* is the fact that the substrates (6) and (6bis) are racemic compounds which contain weakly acidic protons on the chiral carbon atoms. During the asymmetric hydrogenation the chiral catalyst converts at first only one enantiomer of (6) or (6bis). In the mean time, due to the configurational lability of the chiral center, the other enantiomer is racemized in situ by the base. Since the desired enantiomer of (6) and (6bis) to be hydrogenated is generated continuously from the undesired one, finally 100% yield of the single desired enantiomer of the products (7a) or (III-a) or of (7b) or (III-b), depending on the chirality of the catalyst selected, can be obtained.

It has been found that the salt of the piperidine derivative of formula (6) is stable and can be hydrogenated in high optical and chemical yields by the process according to the invention. The hydrogenation may also be performed with the salt of the unprotected piperidine derivative of formula (6bis).

The asymmetric hydrogenation is carried out in presence of a ruthenium phosphine complex represented by the formula $$Ru(E)_2(L)\ (A) \qquad \qquad IV$$

wherein
E is a halogen atom;
L is a chiral diphosphine ligand; and
A is a chiral diamine.

Complexes of type IV can be specifically prepared, isolated and characterized in analogy to the methods described in Angew. Chem. Int. Ed. 1998, 37, 1703–1707 and in the references cited therein, or can be prepared "in situ" from components as described in above mentioned reference, and be employed without intermediate isolation in the catalytic asymmetric hydrogenation. When the complexes of type IV are prepared in situ, the amount of chiral diphosphine ligand (L) used in the reaction can vary from 0.5 to 2.5 equivalents relative to ruthenium, preferably from 0.8 to 1.2 equivalents. Analogously the amount of chiral diamine can vary from 0.5 to 2.5 equivalents based on the amount of the ruthenium-complex, preferably 1 to 2 equivalents.

Suitable chiral diphosphine ligands are known in the art. Such ligands are for example atropisomeric biphenyl-phosphine or binaphthyl-phosphine derivatives. Further ligands which may be useful in the present hydrogenation are 1,2-bis(2,5-dimethylphospholano)benzene as described in U.S. Pat. No. 5,171,892; 1-[2-(diphenylphosphino)ferrocenyl]-ethyl-di-tert.-butyl-phosphine as described in EP 0 564 406; 1-[2-(di-(4-trifluoromethyl)phenyl)-phosphino)ferrocenyl]ethyl-di-phenyl-phosphine as in EP 0 646 590; 4,12-bis(diphenylphosphino)-[2.2]paracyclophane (Tetrahedron Letters 1998, 39, 4441–4444); 4,4'-Bisdiphenylphosphine-2,2',5,5'-tetramethyl-3,3'-dithiophene (WO 96/01831); 2,2-Bis-(diphenylphosphinyl)-3,3'-dibenzo[b]thiophene (WO 96/01831); (2R,2'R)-Bis(diphenylphosphino)-(1R,1'R)-dicyclopentane and enantiomer (WO 97/47633); 1,2-Bis{(1R,2R,4R,5R)-2,5-bis-isopropyl-8-phenylphosphabicyclo [2.2.1]heptyl}benzene and enantiomer (WO 97/47633); 2,2',3,3'-Tetraphenyl-4,4',5,5'-tetramethyl-6,6'-bis-phosphanorborna-2,5-dienyl (Chem Eur Journal 1997,3, 1365–1369); (αR-αR')-2,2'-Bis((α-N,N-dimethylaminopropyl)-(S,S)-1,1'-bis(diphenylphosphino)ferrocene and enantiomer (Tetrahedron: Asymmetry 1999,10, 375–384); and ((5,6),(5',6')-Bis(methylenedioxy)biphenyl-2,2'-diyl)bis(diphenylphosphine) (EP 850945).

Preferably chiral diphosphine ligands of the formulae depicted below are used

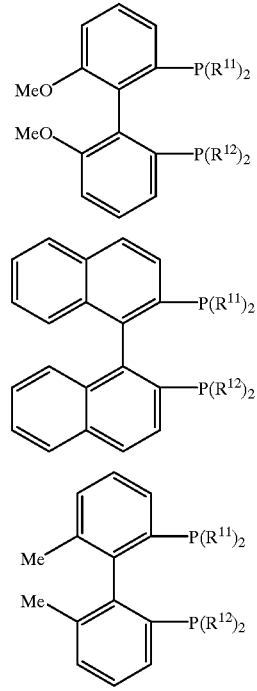

wherein
$R^{11}$ and $R^{12}$ are independently from each other alkyl, cycloalkyl, optionally substituted phenyl or a heterocyclic ring.

Preferred residue $R^{11}$ and $R^{12}$ are

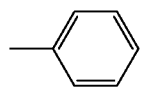

a)

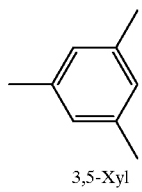

b)

3,5-Xyl

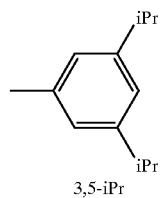

c)

3,5-iPr

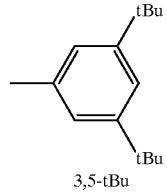

d)

3,5-tBu

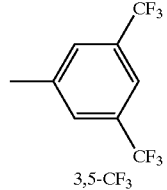

e)

3,5-CF₃

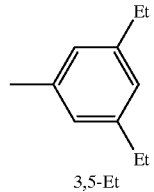

f)

3,5-Et

Especially preferred chiral diphosphine ligands are

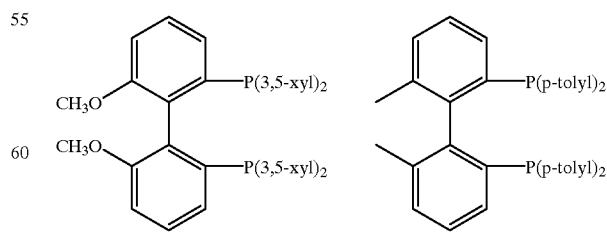

(S)- or (R)-(3,5-Xyl)-MeOBIPHEP    BIPHEMP

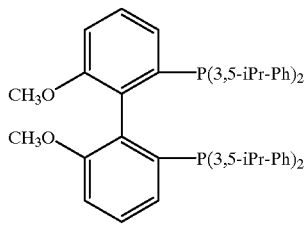

(S)- or (R)-(3,5-iPr)-MeOBIPHEP

Above-mentioned diphosphine ligands are known in the art and can be prepared for example as described in EP 0 398 132 and WO-92/16535 (MeOBIPHEP; 3,5-iPr-MeOBIPHEP), in EP 0 104 375 (BIPHEMP) and in EP 0 580 331 (BINAP).

In order to obtain high yields of the cis-configured product of formula III-a or III-b, in high optical purity it is essential that the reaction be carried out in the presence of a chiral diamine which is in "unlike" configuration to the chiral complex, i.e. it is important that the diphosphine is (S) and the diamine is (R,R) or that the diphosphine is (R) and the diamine is (S,S). In the former case (S diphosphine and R,R diamine), the cis isomer produced is III-a, in the latter case(R diphosphine and S,S diamine) the cis isomer produced is III-b. The reaction is carried out in presence of chiral diamines as depicted below:

V

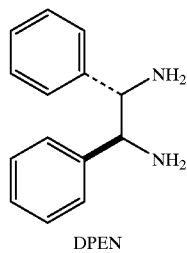

DPEN

VI

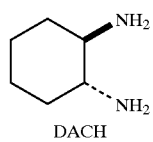

DACH

VII

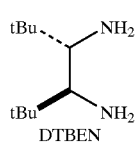

DTBEN

VIII

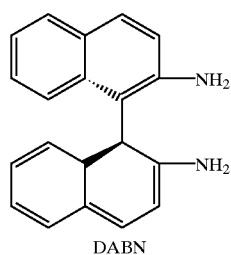

DABN

IX

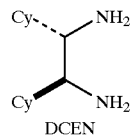

DCEN

X

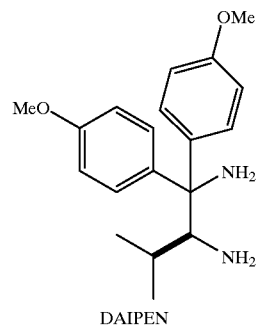

DAIPEN

Further suitable chiral diamines are propane- and butane-diamines. An especially preferred chiral diamine is DPEN (V), (R,R) or (S,S)-1,2-diphenylethylenediamine. The chiral diamines are commercially available or can be prepared according to known methods.

The hydrogenation is preferably carried out in an organic solvent which is inert under the reaction conditions. As such solvents there can be mentioned, in particular, lower alcohols such as e.g. methanol, ethanol or isopropanol, trifluoroethanol or mixtures of such alcohols with halogenated hydrocarbons such as methylene chloride, chloroform, hexafluorobenzene and the like or with ethers such as diethyl ether, tetrahydrofuran or dioxane. Preferred solvent for the reaction are lower alcohols, especially preferred is isopropanol. The reaction is carried out at a concentration of about 1 to 50%, ideally about 5 to 30%.

The substrate-to-catalyst molar ratio (S/C ratio) is 10–1,000,000, preferably 100–800,00. The hydrogenation is carried out at a pressure of $10^5$–$10^8$ Pa, ideally at a pressure of about $10^5$ to $10^7$ Pa and at a temperature of about 0° C. to about 50° C., ideally at 20° C. to 40° C.

Preferred bases used in the asymmetric hydrogenation are for example inorganic or organic bases. Preferred inorganic bases are alkali or alkaline earth metal hydroxides, carbonates, hydrogenocarbonates, alcoholates or silanolates such as for example LiOH, LiOCH$_3$, LiOC$_2$H$_5$, LiOCH(CH$_3$)$_2$, LiOC(CH$_3$)$_3$, NaOH, NaOCH$_3$, NaOC$_2$H$_5$, NaOCH(CH$_3$)$_2$, NaOC(CH$_3$)$_3$, KOH, KOCH$_3$, KOC$_2$H$_5$, KOCH(CH$_3$)$_2$, KOC(CH$_3$)$_3$, KOSi(CH$_3$)$_3$, or Cs$_2$CO$_3$ preferred inorganic bases are alcoholates, especially KOC(CH$_3$)$_3$. Preferred organic bases are tertiary amines such as triethylamine, ethyl-diisopropylamine, tripropylamine and the like.

The amount of organic or inorganic base present in the reaction is about 1.0 to about 0.001, preferably about 0.05 to about 0.2 mol equivalents with respect to the substrate in addition to 1 mol equivalent of organic or inorganic base which is necessary to neutralize the acid salt of the substrate of formula (6) or (6bis), respectively.

The asymmetric hydrogenation of step 5 can be carried out either batchwise or in a continuous manner.

Step 6, deprotection of the compound of formula (7a) or the isomer (7b) under standard conditions depending on the N protecting group, for example by hydrogenation of the N-benzylated compound in presence of Pd/C to form the unprotected amine III-a and III-b, respectively.

Step 6*, refers to the deprotection of the compound of formula (6) in analogy to step 6, to compound (6bis) which is then subsequently submitted to the asymmetric hydrogenation (step 5* discussed above).

Step 7, treating the sulfone intermediate of formula II with a base to form the corresponding vinyl sulfone derivative which is subsequently reacted with the piperidine derivative of formula III-a or III-b to the desired product of formula I-a or I-b, respectively. The reaction is carried out in presence of bases such as triethylamine in solvents such as $CH_2Cl_2$.

As already mentioned previously sulfones of formula II are usually prepared by halogenation of the hydroxy thioether of formula (9) to form the highly toxic and unstable chlorothioether which is then subsequently oxidized to form the intermediate of formula II. The invention now provides a new process to produce this intermediate of formula II, see Scheme 4 which avoids the formation of highly toxic intermediates. The process according to the invention consists of the following steps:

step a), a substituted thiophenyl derivative (8) is deprotonated in presence of a strong inorganic or organic base as defined above and subsequently reacted with 2-haloethanol to form the thioether of formula (9);

step b), oxidation of the thioether (9) in presence of an oxidative agent such as 3-chloroperbenzoic acid (MCPBA), $H_2O_2$/AcOH, $KMnO_4$, tBuOOH, NMO/$OsO_4$, or oxoneo to yield the corresponding sulfone of formula (10); and step c), replacement of the hydroxy group of the sulfone derivative by a halogen atom e.g. with $SOX'_2$, wherein X' is halogen, e.g. chlorine, bromine or iodine in the presence of pyridine in dichloromethane.

The term "pharmaceutically acceptable acid addition salts" embraces salts with inorganic and organic acids, such as hydrochloric acid, nitric acid, sulfuric acid, lactic acid, phosphoric acid, citric acid, formic acid, fumaric acid, maleic acid, acetic acid, succinic acid, tartaric acid, methane-sulfonic acid, p-toluenesulfonic acid and the like.

As used herein, the term "alkyl" refers to both straight and branched chain saturated hydrocarbon groups having 1 to 10 carbon atoms; whereas the term lower alkyl refers to both straight and branched chain saturated hydrocarbon groups having 1 to 5 carbon atoms, for example, methyl, ethyl, n-propyl, isopropyl, tert.-butyl and the like. The term "lower alkoxy" means a lower alkyl group as defined above, bonded through an oxygen atom. Examples are methoxy, ethoxy, n-propoxy, isopropoxy, n-butoxy, tert-butoxy and the like.

The term "lower-alkyl-sulfonylamido" refers to sulfonamido groups substituted with "lower alkyl" groups as defined above.

The term "cycloalkyl" refers to a cyclic hydrocarbon group having 3 to 7 carbon atoms. Such groups are for example cyclopropyl, cyclobutyl, cyclopentyl, cyclohexyl, cycloheptyl and the like.

The term "optionally substituted phenyl" refers to unsubstituted phenyl or mono, di- or trisubstituted phenyl groups with substituents such as lower alkyl, alkoxy groups or halogenated alkyl such as trifluoromethyl, pentafluoroethyl, or substituted with halogen, hydroxy, amino, dialkylamino or acetamido, or substituted with phenyl or trialkylsilyl and the like.

As used herein "heterocyclic ring" refers to 5 or 6-membered rings containing one or two hetero atoms chosen from O, S and N. Examples of preferred heterocyclic rings are furane, thiophene, pyrrole, pyridine and pyrimidine. The heterocyclic rings may be unsubstituted or substituted with substituents as defined for "substituted phenyl".

As used herein the term "leaving group" refers to conventionally used easily substituted functional groups such as halogen, e.g. chlorine, bromine or iodine, or organic acid residues such as sulfonic acid derivatives, e.g. p-toluene sulfonate, brosylate, methylsulfonate, triflate (trifluoromethylsulfonate) and the like.

Nucleophilic substitution of the leaving groups (steps 1 and 7) are carried out by methods known in the art, e.g. in inert organic solvents under basic conditions. "Inert organic solvents" refers to polar solvents such as dimethylformamide (DMF), dimethylacetamide (DMA), dimethylsulfoxide (DMSO), or to alcohols such as methanol, ethanol or isopropanol, or to cyclic ethers such as dioxane or tetrahydrofurane (THF), or to halogenated hydrocarbons such as dichloromethane, or to aromatic hydrocarbons such as toluene, or to nitrites, such as acetonitrile, or to mixtures of the named solvents. As bases are used inorganic or organic bases. Preferred inorganic bases are alkali or alkaline earth metal hydroxides, carbonates, hydrogenocarbonates, alcoholates or silanolates. Preferred organic bases are tertiary amines such as triethylamine, ethyl-diisopropylamine, tripropylamine and the like.

The term "amino protecting group" refers in the scope of the present invention to groups such as those employed in peptide chemistry for example to benzyl, tert.-butoxycarbonyl, allyloxy carbonyl and the like; to a substituted alkoxycarbonyl group such as trichloroethoxycarbonyl etc.; to an optionally substituted aralkyloxycarbonyl group, for example, p-nitrobenzyloxycarbonyl or benzyloxycarbonyl; to an aralkyl group such as trityl or benzhydryl; to an alkanoyl group such as formyl or acetyl; to a halogen-alkanoyl group such as chloroacetyl, bromoacetyl, iodoacetyl or trifluoroacetyl; or to a silyl protective group such as the trimethylsilyl group. Especially preferred amino protecting are benzyl, tert.-butoxycarbonyl (BOC) and benzyloxycarbonyl (Z). For the hydrogenation step (step 5) to be highly enantioselective it is essential that the protected nitrogen is basic, therefore benzyl is an especially preferred protecting group.

The term "carboxylic acid protecting group" refers in the scope of the present invention to protecting groups conventionally used to replace the acidic proton of a carboxylic acid. Examples of such groups are described in Greene, T., Protective Groups in Organic Synthesis, Chapter 5, pp. 152–192 (John Wiley and Sons, Inc. 1981). Preferably these examples include methoxymethyl, methylthiomethyl, 2,2,2-trichloroethyl, 2-haloethyl, 2-(trimethylsilyl)ethyl, methyl, ethyl, isopropyl, tert.-butyl, allyl, benzyl, triphenylmethyl (trityl), benzhydryl, p-nitrobenzyl, p-methoxybenzyl, trimethylsilyl, triethylsilyl, tert.-butyldimethylsilyl, i-propyldimethylsilyl. Preferred are benzhydryl, tert.-butyl, p-nitrobenzyl, p-methoxybenzyl and allyl. Especially preferred carboxylic protecting groups are methyl, ethyl, tert. butyl or benzyl.

Suitable protecting groups and methods for their cleavage will be familiar to any person skilled in the art, although of course there can be used only those protecting groups which can be cleaved off by methods under the conditions of which other structural elements in the compounds are not affected.

The term "oxygen acid or complex acid" signifies in the scope of the present invention acids from the group $H_2SO_4$, $HClO_4$, $HBrO_4$, $HIO_4$, $HNO_3$, $H_3PO_4$, $CF_3SO_3H$ as well as halogen complexes with the elements boron, phosphorus, arsenic, antimony or bismuth. $HClO_4$, $CF_3SO_3H$, $HPF_6$, $HBF_4$, $HB(Ph)_4$, $HB(3,5-(CF_3)_2-C_6H_3)_4$, $HSbF_6$ and $HAsF_6$ are preferred representatives with $HSbF_6$ and $HBF_4$ being most preferred.

The following abbreviations are used in the description of the examples:

| | |
|---|---|
| MeOBIPHEP: | (6,6'-Dimethoxybiphenyl-2,2'-diyl)bis(diphenylphosphine) |
| BIPHEMP: | (6,6'-Dimethylbiphenyl-2,2'-diyl)bis(diphenylphosphine) |
| BINAP: | (1,1'-Binaphthyl)-2,2'-diyl]bis(diphenylphosphine) |
| mTol-MeOBIPHEP: | (6,6'-Dimethoxybiphenyl-2,2'-diyl)bis[bis(m-tolyl)-phosphine] |
| (3,5-Xyl)-MeOBIPHEP: | (6,6'-Dimethoxybiphenyl-2,2'-diyl)bis[bis( 3,5-dimethyl-phenyl)phosphine] |
| (3,5-Et)-MeOBIPHEP: | (6,6'-Dimethoxybiphenyl-2,2'-diyl)bis[bis(3,5-diethyl-phenyl)phosphine] |
| (3,5-iPr)-MeOBIPHEP: | (6,6'-Dimethoxybiphenyl-2,2'-diyl)bis[bis(3,5-diisopropyl-phenyl)phosphine] |
| (3,5-CF$_3$)-MeOBIPHEP: | (6,6'-Dimethoxybiphenyl-2,2'-diyl)bis [bis(3,5-bis(trifluoro-methyl)phenyl)phosphine] |
| (3,5-iPr,4-MeO)-MeOBIPHEP: | (6,6'-Dimethoxybiphenyl-2,2'-diyl)bis [bis (3,5-diisopropyl-4-methoxyphenyl)phosphine] |
| (3,5-Me,4-MeO)-MeOBIPHEP: | (6,6'-Dimethoxybiphenyl-2,2'-diyl)bis [bis(3,5-dimethyl-4-methoxy-phenyl)phosphine] |
| (3,5-tBu)-MeOBIPHEP: | (6,6'-Dimethoxybiphenyl-2,2'-diyl)bis [bis(3,5-tert.butyl-phenyl)phosphine] |
| (3,5-TMS)-MeOBIPHEP: | (6,6'-Dimethoxybiphenyl-2,2'-diyl)bis [bis(3,5-trimethyl-silylphenyl)phosphine] |
| COD | 1,5-cyclooctadiene |
| DPEN: | 1,2-Diphenylethylenediamine |
| DACH: | trans-1,2-Diaminocyclohexane |
| DTBEN: | 1,2-Di-tert.-butylethylenediamine |
| DABN: | 2,2'-Diamino-1,1'-binaphthalene |
| DCEN | 1,2-Dicyclohexane-ethylendiamine |
| DAIPEN | 1,1-Di(p-methoxyphenyl)-2-isopropylethylenediamine |
| S/C: | substrate-to-catalyst molar ratio |
| S/base: | substrate-to-base molar ratio |

The examples below will further illustrate the present invention and are not intended to limit it in any way:

EXAMPLE 1 (STEP 1)

Preparation of 4-(benzyl-ethoxycarbonylmethyl-amino)-butyric acid ethyl ester

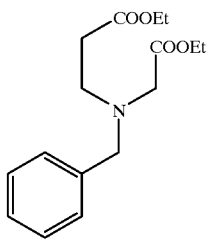

EXAMPLE 1.1

A solution of 4.9 ml (25.8 mmol) N-benzylglycine ethyl ester and 7.7 ml (51.7 mmol) ethyl-4-bromobutyrate in 40 ml dimethylformamide (DMF) was treated at room temperature with 9.0 ml (64.3 mmol) triethylamine. The reaction mixture was heated to 65° C. and stirred for 23 h, subsequently cooled to room temperature and DMF was evaporated. The residue was treated with 100 ml water and 100 ml ethyl acetate. The phases were separated after extraction, the organic phase washed twice with total 100 ml water and the combined organic phase dried over Na$_2$SO$_4$. The solvent was removed under reduced pressure and the residue purified by chromatography over silica gel (hexane: ethyl acetate=9:1) to yield 7.1 g (88.8%) product as yellow oil. MS (ISP): 308 (100, [M+H]$^+$)

EXAMPLE 1.2

To a solution of 2.57 l (17.25 mol) ethyl-4-bromobutyrate in 10 l dioxane was added at 100° C. 1.72 kg (8.54 mol) N-benzylglycine ethyl ester. The reaction mixture was treated under reflux dropwise over a period of 6 h with 3.10 l (22.24 mol) triethylamine and subsequently stirred under reflux for 16 h. The suspension was cooled to 50° C. and treated with 10 l toluene, stirred at 0° C. for 1 h and afterwards filtered. The filtrate was concentrated to yield 3.08 kg crude product.

EXAMPLE 2 (STEP 2)

Preparation of rac-ethyl N-benzyl-3-oxo-4-piperidinecarboxylate hydrochloride

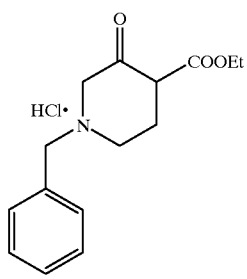

EXAMPLE 2.1

A solution of 2.8 g (9.1 mmol) 4-(benzyl-ethoxycarbonylmethyl-amino)-butyric acid ethyl ester in 18 ml toluene was treated at room temperature with 980.0 mg (13.7 mmol) sodium ethoxide. The reaction mixture was heated to 85° C. and stirred for 3.5 h. After cooling to room temperature the reaction mixture was poured onto 50 ml ice-water, treated with 50 ml toluene and subsequently extracted. The aqueous phase was extracted with total 100 ml ethyl acetate, the organic phase washed twice with total 100 ml water and the combined organic phase dried over Na$_2$SO$_4$. The solvent was removed under reduced pressure to yield 2.2 g crude product. This crude product was treated with 3.7 ml of a solution of HCl in methyl alcohol 20%-weight and subsequently the solvent was removed under reduced pressure to yield 2.4 g crude product as white crystals. The crystals were dissolved under reflux in 30 ml isopropanol and the solution cooled to room temperature and stirred at this temperature for 2 h. The formed crystals were separated on a filter funnel and washed with 3 ml isopropanol (4° C.) and dried to yield 1.8 g (67.5%) product as white crystals. MS (ISP): 262 (100, [M+H]$^+$).

EXAMPLE 2.2

A solution of 2.02 kg (5.60 mol) crude 4-(benzyl-ethoxycarbonylmethyl-amino)butyric acid ethyl ester from Example 1.2. in 10 l toluene was treated at room temperature with 0.79 kg (11.03 mol) sodium ethoxide (exothermic). The reaction mixture was heated to 85° C. and stirred for 3.5 h. The so formed suspension was cooled to room temperature and treated with 5 l toluene and 0.5 kg dicalite speedex. After neutralization by slowly addition of 0.7 l acetic acid the suspension was filtered. The filtrate was concentrated to a volume of 9 l and treated with 1.4 l (6.86 mol) HCl in ethanol (4.9 M). After formation of crystals the ethanol was exchanged under reduced pressure by addition of 8 l toluene. The so formed suspension was treated with 5 l toluene, stirred at 0° C. for 16 h and subsequently filtered. The crystals were dried to yield 1.62 kg (94%) product.

EXAMPLE 3 (STEP 3)

Preparation of rac-1,4-dibenzyl-3-oxo-piperidine-4-carboxylic acid ethyl ester

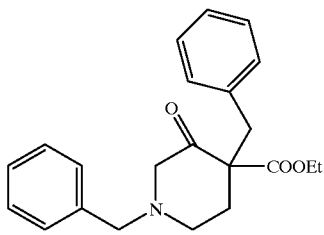

A mixture of 38.3 g (341.0 mmol) potassium tert.-butoxide and 625 ml absolute tetrahydrofuran was stirred at room temperature for 0.5 h. The resulting milky solution was cooled to 0° C. and then 50.0 g (168.0 mmol) ethyl N-benzyl-3-oxo-4-piperidine carboxylate hydrochloride were added via a powder dropping funnel. The temperature was kept below 5° C. The mixture was warmed up to room temperature and further stirred for 1 h resulting in a yellow solution. After cooling to 0° C., a solution of 30.2 g (176.0 mmol) benzyl bromide in 20.0 ml of absolute tetrahydrofuran was dropwise added in 0.5 h. A maximum temperature of 2° C. was observed. The reaction mixture was warmed to room temperature and stirred for 4 h. The reaction solution was cooled to 0° C. and 200 ml saturated ammonium chloride solution was slowly added. After extraction and phase separation, the aqueous phase was extracted twice with 100 ml of ethyl acetate. The combined organic phase were washed twice with 100 ml of saturated sodium chloride solution, dried over Na$_2$SO$_4$, the solvent evaporated under reduced pressure and the residue dried to yield 58.3 g (99.3%) crude product. MS (ISP): 352 (100, [M+H]$^+$), 174 (15).

EXAMPLE 4 (STEP 4)

Preparation of rac-1,4-dibenzyl-3-oxo-piperidine hydrochloride

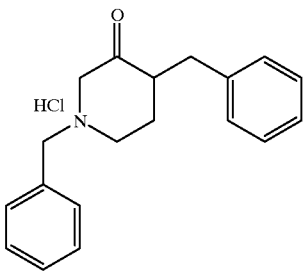

A solution of 118.0 g (336 mmol) crude rac-1,4-dibenzyl-3-oxo-piperidine-4-carboxylic acid ethyl ester in 118.0 ml of absolute ethanol was cooled to 0° C. and subsequent 405 ml (4.9 mol) 37% hydrochloric acid was cautiously added. The reaction temperature was kept below 7° C. Finally the mixture was heated under reflux for 19 h. To the dark brown solution were added some crystals of rac-1,4-dibenzyl-3-oxo-piperidine hydrochloride, then the mixture was allowed to cooled to room temperature and further stirred for 2 h. The resulting crystals, after recuperation on a Buchner funnel and washing twice with 60 ml of deionized water, were dried to yield 102.2 g crude product. Then 400 ml of ethyl acetate was added to the crude product and the mixture refluxed for 2 h and cooled afterwards to room temperature. The resulting beige suspension was filtered, the crystals were washed twice with 50 ml of ethyl acetate and dried to yield 82.2 g (78% over two steps) product. MS (ISP): 280 (100, [M+H]$^+$), 262 (9). M.p. 202–203° C.

EXAMPLE 5 (STEP 5)

Preparation of cis-1,4-dibenzyl-3-hydroxy-piperidine

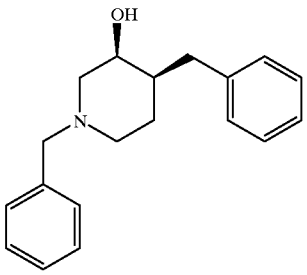

EXAMPLE 5.1

In the glove box (O$_2$ content<=2 ppm) a 20 ml measuring flask was charged with is 14.03 mg of [RuCl$_2$((S)-3,5-Xyl-MeOBIPHEP)((R,R)-DPEN)] (0.050 mmol) and filled to the graduation mark with 20 ml of isopropanol. The clear yellow catalyst solution was stirred with a magnetic stirring bar for 20 min at room temperature. The Ru-complex had been prepared by reaction of (S)-3,5-Xyl-MeOBIPHEP, [RuCl$_2$(COD)]$_n$, and (R,R)-DPEN in analogy to Angew. Chem. Int. Ed. 1998, 37, 1703–1707. In the glove box a glass flask was charged with 41.06 g (0.130 mol) of 1,4-dibenzyl-piperidin-3-one hydrochloride, 205 ml of isopropanol and 17.51 g (0.156 mol) of potassium tert.-butylate. The resulting suspension was stirred for 10 min and transferred into a 380 ml stirred stainless steel autoclave followed by 4.0 ml of catalyst solution, S/C=50,000. The autoclave was then sealed and connected to a hydrogenation line. The hydrogenation was carried out while stirring at room temperature at a total pressure of $4\times10^6$ Pa. After 3 h the hydrogenation mixture (a yellow suspension) was removed from the autoclave. A sample thereof was filtered, evaporated to dryness and analyzed as follows:

a) A 25-mg sample was dissolved in 0.8 ml of pyridine and silylated with 0.2 ml of commercial N,O-bis-(trimethylsilyl)-acetamide (BSA)+5% trimethylchlorosilane (TMS)-solution. Gas chromatographic analysis on a Permaphase PVMS/54 column showed complete conversion and a cis/trans ratio of 99:1. Retention times: 10.65 min (trans-1,4-dibenzyl-piperidin-3-ol), 10.80 min (cis-1,4-dibenzyl-piperidin-3-ol), 11.15 min (rac-1,4-dibenzyl-piperidin-3-one).

b) ca. 0.6 ml sample of reaction mixture was taken up in water/ethyl acetate mixture and treated with a 5% ammonium chloride solution. The organic phase was dried ($Na_2SO_4$). HPLC analysis of an aliquot containing ca. 5–10 mg of product confirmed that the cis/trans-ratio was 99:1 and showed the enantiomeric purity (ee) of (S,S)-cis-1,4-dibenzyl-piperidin-3-ol to be 91%. Column: 2× Chiralpak AS, (250×4.6 mm), Daicel Chemicals Industries, Cat. No.20025; Mobile phase: 1% (v/v) ethanol in n-hexane; flow 1.2 ml/min; pressure $6\times10^5$ Pa. The following retention times were observed: 11.2 min cis-(R,R)-product; 12.5 min cis-(S,S)-product; 17.5 and 19.5 min starting material (two enantiomers), 17.5 and 19.5 min trans-product (two enantiomers).

EXAMPLE 5.2

(scaled-up)

In the glove box ($O_2$ content<=2 ppm) a 100 ml measuring flask was charged with 68.3 mg of [$RuCl_2$((S)-3,5-Xyl-MeOBIPHEP)((R,R)-DPEN)] (0.0633 mmol) and filled to the graduation mark with isopropanol. The clear yellow catalyst solution was stirred with a magnetic stirring bar for 20 min at room temperature and then transferred into a catalyst addition device. A 12-L Hastelloy C4 stirred autoclave was charged with 1.00 kg (3.17 mol) of rac-1,4-dibenzyl-piperidin-3-one hydrochloride, 5 l of isopropanol and 426.36 g (3.8 mol) of potassium tert.-butylate and sealed, S/C=50,000. The autoclave was then sealed, the atmosphere was exchanged with argon and finally the autoclave was connected to a hydrogenation line. The hydrogenation was carried out while stirring at room temperature at a total pressure of $4\times10^6$ Pa. After 4 h the hydrogenation mixture (a yellow suspension) was removed from the autoclave. A sample thereof was filtered, evaporated to dryness and analyzed as described in Example 5.1: complete conversion, cis/trans product 99.1:0.6, 91% ee (cis-product with (S,S)-configuration).

EXAMPLES 5.3–5.12

The experiments in Table 1 have been carried out in analogy to Example 5.1 using various chiral diphosphines with S-configuration.[a]

TABLE 1

| exp. no. | (S)-Diphosphines | S/C | S/base[c] | % Conv./h | cis/trans % | % ee[e] |
|---|---|---|---|---|---|---|
| 5.3 | MeOBIPHEP | 500 | 1.25 | 100/2.5 | 98/2 | 76 |
| 5.4[d] | BIPHEMP | 100 | 5 | 100/2.5 | 99/1 | 75[f] |
| 5.5[d] | BINAP | 100 | 5 | 100/2.5 | 98/1 | 74 |
| 5.6[b] | (3,5-iPr)-MeOBIPHEP | 2000 | 5 | 100/2 | 99/1 | 96 |
| 5.7[d] | (3,5-CF3)-MeOBIPHEP | 1000 | 2.5 | 100/3 | 99/1 | 90 |
| 5.8[b,d] | (3,5-Et)-MeOBIPHEP | 2000 | 5 | 100/3 | 99/1 | 95 |
| 5.9[d] | (mTol)-MeOBIPHEP | 1000 | 2.5 | 100/3 | 99/1 | 82 |
| 5.10[b] | (3,5-TMS)-MeOBIPHEP | 2000 | 5 | 27/3 | 83/17 | 71 |
| 5.11[d] | (3,5-iPr,4-MeO)-MeOBIPHEP | 1000 | 2.5 | 58/3 | 89/11 | 40 |
| 5.12 | (3,5-tBu)-MeOBIPHEP | 1000 | 2.5 | 100/21 | 88/12 | 36 |

[a] 185 ml autoclave, 1.3 g scale, c = 5%.
[b] 185 ml autoclave, 10 g scale, c = 10%.
[c] In addition to 1 molar equivalent for the neutralization of the hydrochloride.
[d] Ruthenium complex prepared in situ from [$RuCl_2$(diphosphine)(DMF)$_n$] + DPEN.
[e] of the cis-product with (S,S)-configuration.
[f] Ruthenium complex prepared in situ from [RuCl((S)-BIPHEMP)(benzene)]Cl and (R,R)-DPEN

EXAMPLES 5.13–5.15

The experiments in Table 2 have been carried out under following conditions: 185-ml autoclave, 1.3 g scale, c=5% in isopropanol, 20° C., $4\times10^6$ Pa hydrogen. The ruthenium catalyst has been prepared in the glove box by stirring the complex [$RuCl_2$((S)-(3,5-Xyl)-MeOBIPHEP)(DMF)$_n$] with 1 molar equiv. of chiral diamine at room temperature for 1 h.

TABLE 2

| Exp. No. | Chiral diamine | S/C | S/base | % Conv./h | cis/trans % | % ee[a] |
|---|---|---|---|---|---|---|
| 5.13 | (R,R)-DPEN | 1000 | 2.5 | 100/4 | 99/1 | 90 |
| 5.14 | (R,R)-DTBEN | 100 | 0.25 | 100/4 | 99/1 | 73 |
| 5.15 | (R,R)-DACH | 1000 | 2.5 | 100/3 | 99/1 | 87 |

[a] ee of the cis-product with (S,S)-configuration.

EXAMPLES 5.16–5.22

The experiments in Table 3 have been carried out in analogy to Example 5.1 using various conditions. Catalyst: [$RuCl_2$((S)-3,5-Xyl-MeOBIPHEP)((R,R)-DPEN)], base: KOtBu, S/base=5[c], 185 ml autoclave, 9.5 g scale.

TABLE 3

| Exp. No. | P (Pa) | S/C | Conc. (%) | % Conv./h | cis/trans % | % ee[d] |
|---|---|---|---|---|---|---|
| 5.16 | $5 \times 10^5$ | 2000 | 10 | 100/22 | 99/1 | 88 |
| 5.17 | $8 \times 10^6$ | 2000 | 10 | 100/2 | 99/1 | 91 |
| 5.18[b] | $4 \times 10^6$ | 2000 | 20 | 100/2 | 99/1 | 91 |
| 5.19[a] | $4 \times 10^6$ | 2000 | 30 | 100/5 | 99/1 | 90 |
| 5.20 | $2 \times 10^7$ | 800,000 | 20 | 100/4 | 99/1 | 89 |
| 5.21[e] | $4 \times 10^6$ | 400,000 | 20 | 98/4 | 99/1 | 90 |
| 5.22[e] | $4 \times 10^6$ | 800,000 | 20 | 99/20 | 99/1 | 87 |

[a] 185 ml autoclave, 32 g scale;
[b] 380 ml autoclave, 41 g scale;
[c] In addition to 1 molar equivalent for the neutralization of the hydrochloride;
[d] ee of the cis-product with (S,S)-configuration;
[e] S/base = 10.

EXAMPLE 5.23

In a manner analogous to Example 5.1, 41.06 g of rac-1,4-dibenzyl-piperidin-3-one hydrochloride was asymmetrically hydrogenated in the presence of 1.4 mg of [RuCl$_2$((S)-3,5-iPr-MeOBIPHEP)((R,R)-DPEN)], S/C=100,000 for 16 hours to afford after work-up (S,S)-cis-1,4-dibenzyl-piperidin-3-ol of 97% ee.

EXAMPLE 5.24

In a manner analogous to Example 5.23, but at a temperature of 30° C., 41.06 g of rac-1,4-dibenzyl-piperidin-3-one hydrochloride was asymmetrically hydrogenated in the presence of 3.0 mg of [RuCl$_2$((S)-3,5-iPr-MeOBIPHEP)((R,R)-DPEN)], S/C=50,000, to afford after work-up (S,S)-cis-1,4-dibenzyl-piperidin-3-ol of 96% ee.

EXAMPLES 5.25–5.28

The experiments in Table 4 have been carried out under the following conditions: 30 ml autoclave, 0.45 g of rac-1,4-dibenzyl-piperidin-3-one, c=10% in isopropanol, 20° C., $4 \times 10^6$ Pa hydrogen. Catalyst: [RuCl$_2$((S)-3,5-iPr-MeOBIPHEP)((R,R)-DPEN)], S/C=300, S/base=5 (in addition to 1 molar equivalent for the neutralization of the hydrochloride).

TABLE 4

| Exp. No. | Base | % Conv./h | Cis/trans % | % ee[a] |
|---|---|---|---|---|
| 5.25 | NaOC(CH$_3$)$_3$ | 100/16 | 99/1 | 95 |
| 5.26 | KOSi(CH$_3$)$_3$ | 100/18 | >99/1 | 76 |
| 5.27 | KOCH$_3$ | 100/18 | >99/1 | 91 |
| 5.28 | Cs$_2$CO$_3$ | 95/18 | 99/1 | 87 |

[a] ee of cis-product with (S,S)-configuration.

EXAMPLES 5.29–5.32

The experiments in Table 5 have been carried out under the following conditions: 185-ml autoclave, 9.5 g scale, mixture of isopropanol (23 ml) and a co-solvent (23 ml), 20° C., $4 \times 10^6$ Pa hydrogen. Catalyst: [RuCl$_2$((S)-3,5-iPr-MeOBIPHEP) ((R,R)-DPEN)], S/C=50,000, S/KOC(CH$_3$)$_3$=5 (in addition to 1 molar equivalent for the neutralization of the hydrochloride).

TABLE 5

| Exp. No. | Co-solvent | % Conv./h | Cis/trans % | % ee |
|---|---|---|---|---|
| 5.29 | Toluene | 74/20 | 86/14 | 90 |
| 5.30 | CH$_3$CO$_2$Et | 87/20 | 98/2 | 97 |
| 5.31 | CH$_2$Cl$_2$[b] | 100/20 | 98/2 | 95 |
| 5.32 | THF | 89/20 | 86/14 | 93 |

[a] ee of cis-product with (S,S)-configuration.
[b] Mixture of isopropanol (18 ml) and CH$_2$Cl$_2$ (18 ml).

EXAMPLE 6 (STEP 6)

Preparation of (3S, 4S)-4-benzyl-piperidine-3-ol (work-up after hydrogenation and deprotection of the amino group)

EXAMPLE 6.1

The reaction mixture from Example 5.1 was treated with 300 ml ethyl acetate, 170 ml water, 50 ml 5% aqueous NH$_4$Cl solution and solid NaCl to saturate the aqueous phase. After phase separation, the aqueous phase was extracted twice with 200 ml ethyl acetate and the organic phases were washed twice with 150 ml brine. The combined organic phase was dried over Na$_2$SO$_4$, the solvent evaporated under reduced pressure to yield 35.6 g crude material as light-yellow crystals. This material was dissolved in 400 ml ethanol, treated at room temperature with 6.7 g (6.3 mmol) Pd/C 10% and stirred under H$_2$ at 55° C. for 2 h. Subsequent filtration and evaporation of the solvent yielded 25.3 g crude product as amorphous material. This crude product was dissolved at 100° C. in 100 ml toluene, cooled to 65° C. and treated with 125 ml hexane. The so formed suspension was cooled to 35° C. and treated again with 125 ml hexane. The suspension was stirred for 48 h at 0° C. and filtered afterwards to yield 10.0 g (ee=99.8%) product as white crystals. The mother liquor (13.9 g) was dissolved at 90° C. in 45 ml toluene treated at 55° C. with 55 ml hexane, cooled to 45° C. and added again 55 ml hexane. The suspension was stirred 16 h at room temperature and 3 h at 0° C., filtered to yield 9.7 g (ee=99.9%) product as white crystals. (Overall yield 81.5%) MS (EI): 191 (100, [M]), 118 (76), 91 (44), 30 (100). M.p. 91.5–92.5° C.

EXAMPLE 6.2

(work-up after hydrogenation, deprotection of the amino group and crystallization in presence of a resolving agent)

The reaction mixture from Example 5.1 was treated with 10 ml 5% aqueous NH$_4$Cl solution and concentrated under reduced pressure to a total volume of 50 ml. This residue was treated with 50 ml water, 16 g NaCl, 50 ml 5% aqueous NH$_4$Cl solution and extracted twice with 100 ml ethyl acetate. The organic phases were washed twice with 100 ml brine, the combined organic phase was dried over Na$_2$SO$_4$ and the solvent evaporated under reduced pressure. The residue was dissolved in 105 ml ethanol, treated at room temperature with 1.8 g (1.7 mmol) Pd/C 10% and stirred under H$_2$ at 55° C. for 2.5 h. Subsequent filtration and evaporation of the solvent yielded 6.2 g crude product as yellow oil. The crude product was dissolved in 180 ml methanol and treated at 65° C. with a solution of 6.2 g (15.73 mmol) of (+)-di-O,O'-p-tolyl-D-tartaric acid in 25 ml methanol. The suspension was cooled to room temperature, stirred 48 h at this temperature, cooled to 0° C. and stirred for 2 h.

The suspension was filtered to yield 9.2 g (ee=98.9%) salt as white crystals. 9.09 g of this product was dissolved in 460 ml methanol, stirred 1 h under reflux, cooled slowly to room temperature and stirred for 16 h at room temperature The suspension was cooled to 0° C., treated with 460 ml diethyl ether and stirred for 3 h. The suspension was filtered to yield 8.65 g (72.5%) salt. 4.02 g of this salt was dissolved in 40 ml CH$_2$Cl$_2$ and treated with 20 ml aqueous NaOH 1N. After extraction and phase separation, the aqueous phase was extracted twice with 20 ml CH$_2$Cl$_2$ and the combined organic phase dried over Na$_2$SO$_4$. The solvent was removed under reduced pressure to yield 2.0 g (100%, ee=99.6%) product. Overall yield was 72.5%.

EXAMPLE 7 (STEP 7)

Preparation of (3S,4S)-4-benzyl-1-[2-(4-hydroxy-benzenesulfonyl)-ethyl]-piperidin-3-ol

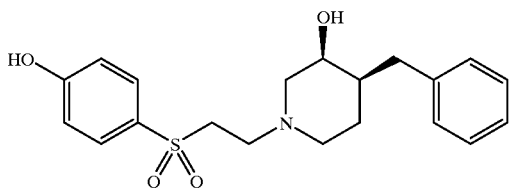

EXAMPLE 7.1

A solution of 5.5 g (24.4 mmol) 4-(2-chloro-ethane-sulfonyl)-phenol in 50 ml CH$_2$Cl$_2$ was treated at 37° C. with 3.7 ml (26.4 mmol) triethylamine and stirred for 3.25 h. Afterwards a solution of 4.5 g (22.0 mmol) (3S, 4S)-4-benzyl-piperidin-3-ol in 40 ml CH$_2$Cl$_2$ was added over a time period of 15 min. The reaction mixture was stirred at 37° C. for 3 h, cooled to room temperature treated with 80 ml water and solid NaCl. After extraction and phase separation the water phases were extracted 3 times with 70 ml CH$_2$Cl$_2$. The combined organic phase was dried over Na$_2$SO$_4$, concentrated to a volume of 70 ml, treated with 75 ml toluene and concentrated to a volume of ca. 100 ml. After 3 d at 0° C. the suspension was concentrated to 50 ml and filtered to yield 9.2 g crude product as white crystals. Chromatographic purification on SiO$_2$ (CH$_2$Cl$_2$/tert.-butylmethyl ether (tBME)=19/1) yielded 7.2 g (87.1%) product as white powder.

MS (ISP): 398 (8, [M+Na]$^+$), 376 (100, [M+H]$^+$), 358 (12).

M.p. 155.5–156.2° C.

EXAMPLE 7.2

As in example 7.1. but instead of chromatographic purification, the crude product is purified by crystallization (dissolving in methanol, afterwards exchange methanol by toluene).

EXAMPLE 8

(step a of Scheme 4)

Preparation of 4-(2-hydroxy-ethylsulfanyl)-phenol

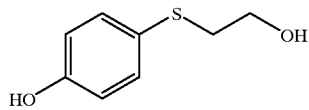

A solution of 5.0 g (35.7 mmol) 4-mercaptophenol in 50 ml methyl alcohol was treated at −5° C. dropwise over a period of 30 min with 39.2 ml (39.2 mmol) aqueous NaOH 1N and stirred 1 h at −5° C. Afterwards a solution of 5.2 ml (39.2 mmol) 2-bromo ethanol in 16.5 ml methyl alcohol was added at −5° C. dropwise over a period of 15 min. The reaction mixture was stirred for 21 h at room temperature, concentrated and the residue treated with 10 ml water and 30 ml tBME. After extraction and phase separation, the organic phase was washed with 20 ml saturated NaHCO$_3$ and 20 ml brine. The combined organic phases were dried over Na$_2$SO$_4$ and the solvent was removed under reduced pressure to yield 6.03 g crude product. The crude product was dissolved in 18 ml tBME at 40° C. and subsequently treated dropwise with 25 ml hexane. The so formed suspension was stirred 16 h at room temperature and 1 h at 4° C. The crystals were separated on a filter funnel and washed with 5 ml hexane (4° C.) to yield 4.8 g (77.7%) product as white crystals.

MS (ISN): 229 (100, [M+OAc]$^-$), 169 (29, [M–H]$^-$).

M.p.: 71.5–72.0° C.

EXAMPLE 9

(step b of Scheme 4)

Preparation of 4-(2-hydroxy-ethansulfonyl)-phenol

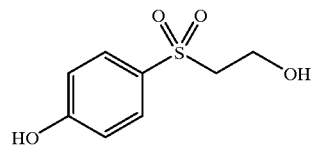

A solution of 5.0 g (28.5 mmol) 4-(2-hydroxy-ethylsulfanyl)-phenol in 25 ml methyl alcohol was treated at 10° C. in parts over 20 min with 26.3 g (42.8 mmol) oxone®. The suspension was stirred at room temperature (exothermic reaction) for 2 h, filtrated and the filtrate treated with 1 ml aqueous sodium hydrogen sulfite solution (38–40%). The pH of the reaction mixture was adjusted to 7 with 2 ml aqueous NaOH (28%), the suspension filtrated and the filtrate evaporated. The residue was treated with 20 ml toluene and subsequent the solvent evaporated. This procedure was repeated two times to yield 6.81 g crude product as white crystals.

MS (EI): 202 (9, [M]), 174 (13), 157 (30), 109 (32), 94 (100)

M.p.: 125.9–127.6° C.

EXAMPLE 10

(step c of Scheme 4)

Preparation of 4-(2-chloro-ethansulfonyl)-phenol

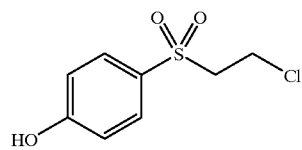

A solution of 6.81 g crude 4-(2-hydroxy-ethansulfonyl)-phenol in 35 ml CH$_2$Cl$_2$ was treated at room temperature with 5.3 ml (65.9 mmol) pyridine. To the reaction mixture was added at 0° C. dropwise over 15 min a solution of 4.2 ml (57.1 mmol) thionyl chloride in 10 ml CH$_2$Cl$_2$. After 65 h at room temperature the reaction mixture was treated with 35 ml brine, extracted and the organic phases were washed twice with total 100 ml aqueous half saturated NaCl solution. The combined organic phases were dried over $Na_2SO_4$ and the solvent was removed under reduced pressure to yield 6.77 g crude product. The crude product was dissolved in 2.5 ml $CH_2Cl_2$ and 25 ml toluene, stirred 24 h at 50° C.) 24 h at room temperature and 48 h at 0° C. The so formed suspension was filtered to yield 5.44 g (86.5% over 2 steps) product as white crystals.

MS (EI): 220 (17, [M]), 157 (100), 109 (18), 94 (17), 93 (60), 65 (41).

M.p.: 72.5–73.5° C.

EXAMPLE 11

(step 6* of Scheme 1)

Preparation of rac-4-benzyl-pyperidine-3-one hydrochloride

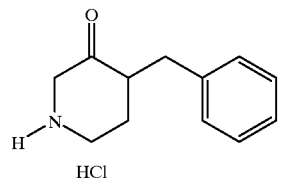

HCl

A suspension consisting of 50.0 g of rac-1,4-dibenzyl-3-oxo-piperidine hydrochloride (0.158 mol), 0.50 l of water and 10.0 g of 5% palladium on charcoal (Pd/C) was stirred under a hydrogen atmosphere until 3.5 l of gas had been consumed (1 h). Then the Pd/C was filtered off and rinsed with water, the filtrate was evaporated and the residue taken up in isopropanol. The crystallization started spontaneously and was completed at 5° C. over night. The precipitate was filtered off, the filter cake was rinsed with cold isopropanol and dried to constant weight (0.2 mbar, room temperature, 2 h) to afford 30 g of rac-4-benzyl-pyperidine-3-one hydrochloride as light yellow crystals. Elemental analysis:

| C | H | N | Cl | (%) |
|---|---|---|---|---|
| 63.86 | 7.15 | 6.212 | 15.71 | (calc) |
| 63.91 | 7.21 | 6.25 | 15.59 | (found) |

EXAMPLE 12

(step 5* of Scheme 1)

Preparation of (S,S)-cis-4-benzyl-3-hydroxy-piperidine

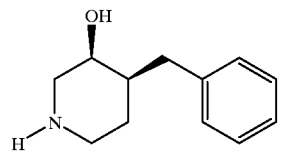

EXAMPLE 12.1

In the glove box ($O_2$ content<=2 ppm) a 20 ml measuring flask was charged with 7.82 mg of [$RuCl_2$((S)-(3,5-iPr)-MeOBIPHEP)((R,R)-DPEN)] (0.0060 mmol) and filled to the graduation mark with 20 ml of isopropanol. The clear yellow catalyst solution was stirred with a magnetic stirring bar for 20 min at room temperature. In the glove box a glass flask was charged with 40.63 g (0.180 mol) of rac-4-benzyl-pyperidine-3-one hydrochloride, 187 ml of isopropanol and 24.24 g (0.216 mol) of potassium tert.-butylate. The resulting suspension was stirred for 15 min and transferred into a 380 ml stirred stainless steel autoclave followed by the catalyst solution, S/C=30,000. The autoclave was then sealed and connected to a hydrogenation line. The hydrogenation was carried out while stirring at room temperature at a total pressure of $4 \times 10^6$ Pa. After 22 h the hydrogenation mixture (a yellow suspension) was removed from the autoclave and filtered. To the orange filtrate were added 2.07 ml of acetic acid and 3.44 g of active charcoal (CPL). The suspension was stirred under argon for 1 h at room temperature and filtered. The yellow filtrate was evaporated to dryness at 42° C. and 1 mbar. The yellow solid residue was taken up in 600 ml of tert.butyl methylether and extracted in 270 ml of 1N HCl (0.27 mol). The acidic aqueous phase washed with 300 ml of tert.butyl methylether and finally treated with 46.3 ml of 28% NaOH solution (0.324 mol), so that the pH was 11. The aqueous phase was extracted with a total of 1 l tert.butyl methylether and the ether phase extracted with 0.60 l of brine, dried on sodium sulfate and finally evaporated to dryness at 42° C. and 1 mbar. The residue was taken up in 100 ml of toluene and again evaporated to dryness to give 34.69 g of crude (S,S)-cis-4-benzyl-3-hydroxy-piperidine with 96.8% ee and a cis/trans-ratio of 98.6: 1.4. Crystallization of the crude product from 120 ml of toluene and 300 ml of hexane at 0° C. afforded after filtration and drying at 40° C./1 mbar 19.35 g of (S,S)-cis-4-benzyl-3-hydroxy-piperidine as off-white crystals with a m.p. of 86–88° C. The samples were analyzed as follows:

A 20 mg sample was transformed into its trifluoroacetate by treatment with trifluoroacetic anhydride in pyridine and analyzed by gas chromatography on a chiral column (BGB-174, commercially available from BGB Analytic AG, Laufrainweg 139, CH-4469 Anwil, 15 m×0.25 mm, 1000–220° C., programmed with 2° C./min). Retention times: 35.19 min (R,R)-cis-4-benzyl-3-hydroxy-piperidine, 35.78 min (S,S)-cis-4-benzyl-3-hydroxy-piperidine, 37.87 and 39.20 min trans-4-benzyl-3-hydroxy-piperidine.

EXAMPLE 12.2

The examples of Table 6 have been carried out in analogy to Example 12.1 in a 35 ml autoclave on a 0.34 g scale at a substrate-to-catalyst ratio of 300 (Exp. No. 12.2.1–12.2.4) or in a 185 ml autoclave on a 9 g scale at a substrate-to-catalyst ratio of 50,000 (Exper. No.12.2.5–12.2.7) using various chiral diphosphines with S-configuration.

TABLE 6

| exp. No. | (S)-Diphosphines | S/base[c] | % Conv./h | cis/trans % | % ee[d] |
|---|---|---|---|---|---|
| 12.2.1 | MeOBIPHEP | 5 | 100/16 | 7/3 | 66 |
| 12.2.2 | (3,5-Xyl)-MeOBIPHEP[a] | 5 | 100/16 | 94/6 | 70 |
| 12.2.3 | (3,5-Xyl)-MeOBIPHEP[b] | 5 | 100/16 | 97/3 | 83 |
| 12.2.4 | (3,5-tBu)-MeOBIPHEP | 5 | 99/16 | 97/3 | 87 |
| 12.2.5 | (3,5-iPr)-MeOBIPHEP | 5 | 99/4 | 98/2 | 97 |
| 12.2.6 | (3,5-Et)-MeOBIPHEP | 5 | 99/20 | 99/1 | 95 |
| 12.2.7 | (3,5-Xyl)-MeOBIPHEP | 5 | 99/4 | 98/2 | 92 |

[a] Catalyst: $RuCl_2$((S)-(3,5-Xyl)-MeOBIPHEP)((S,S)-DPEN)
[b] The diphosphine employed in this experiment was racemic.
[c] In addition to 1 molar equivalent for the neutralization of the hydrochloride.
[d] of the cis-product with (S,S)-configuration.

EXAMPLE 12.3

The examples of Table 7 have been carried out in analogy to Example 12.1 in a 185 ml autoclave on a 9 g scale at 20° C., under 40 bar of hydrogen pressure, at a 20% concentration, for 20 h, with S/base=5 (base was KOtBu) and a S/C=50,000 using [RuCl$_2$((S)-(3,5-iPr)-MeOBIPHEP) ((R,R)-DPEN)] as the catalyst. Various parameters have been changed.

TABLE 7

| exp. no. | Changed parameter | Value | % Conv. | cis/trans % | % ee[a] |
|---|---|---|---|---|---|
| 12.3.1 | S/C | 200'000 | 95 | 95/5 | 95 |
| 12.3.2 | Temperature | 80° C. | 100 | 73/27 | 43 |
| 12.3.3 | H$_2$ Pressure | 20 × 10$^6$ bar | 99 | 98/2 | 97 |
| 12.3.4 | S/base | 50 | 99 | 99/1 | 97 |
| 12.3.5 | Addition of H$_2$O | 0.05 mol | 94 | 98/2 | 96 |
| 12.3.6 | Concentration | 10.6% | 100 | 98/2 | 97 |
| 12.3.7 | Diphosphine Diamine | (S)-(3,5-Xyl)-MeOBIPHEP (S)-DAIPEN | 99 | 94/6 | 95 |
| 12.3.8 | Diphosphine Diamine | (R)-(3,5-Xyl)-MeOBIPHEP (S)-DAIPEN | 99 | 96/4 | 95[b] |

[a] of the cis-product with (S,S)-configuration.
[b] This cis product has (R,R)-configuration.

What is claimed is:
1. A process for the preparation of compounds of formulae

I-a

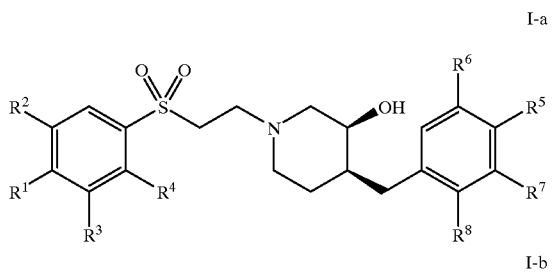

I-b

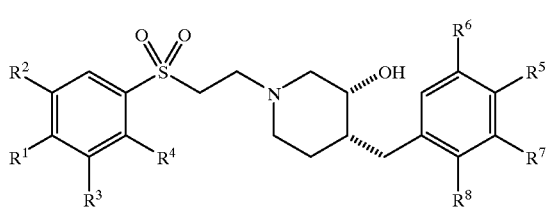

wherein
  R$^1$–R$^4$ are, independently from each other, hydrogen, halogen, hydroxy, amino, nitro, lower-alkyl-sulfonylamido, or acetamido;
  R$^5$–R$^8$ are, independently from each, other hydrogen, lower-alkyl, halogen, trifluoromethyl or lower-alkoxy;
and their pharmaceutically acceptable acid addition salts;
which process comprises
  a) reacting a protected amino acid ester (1)

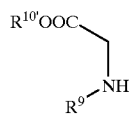

with a 4-substituted butyric acid derivative (2)

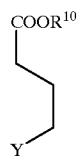

wherein
  R$^9$ is an amino protecting group, preferably benzyl;
  R$^{10}$ and R$^{10'}$ are independently a carboxylic acid protecting group; and
  Y represents a leaving group;
in the presence of a base to obtain the protected alkoxycarbonylmethyl amino butyric acid derivative (3);
  b) cyclising the protected alkoxycarbonylmethyl amino butyric acid derivative (3)

(3)

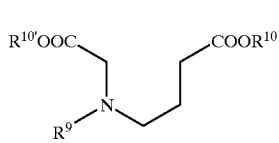

wherein the symbols are as defined above to obtain the protected alkyl 3-oxo-piperidine carboxylate salt (4);
  c) benzylating the protected alkyl 3-oxo-piperidine carboxylate salt (4)

(4)

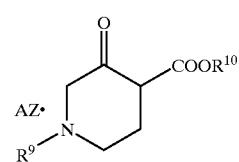

wherein
  AZ signifies a mineral acid or a strong organic acid to obtain the benzylated protected alkyl 3-oxo-piperidine carboxylate (5);
  d) decarboxylating the benzylated protected alkyl 3-oxo-piperidine carboxylate (5)

(5)

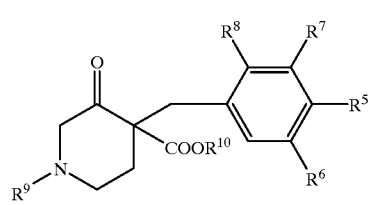

wherein the symbols are as defined above;
in presence of a strong acid to obtain the salt of formula (6);
  e) asymmetrically hydrogenating the salt of formula (6)

(6)

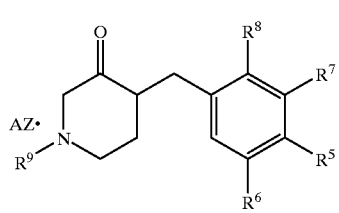

wherein R$^9$ is an amino protecting group;

in presence of a ruthenium complex with a chiral diphosphine ligand and a chiral diamine, wherein the diphosphine has an (S) configuration and the diamine has an (R,R) configuration or the diphosphine has an (R) configuration and the diamine has an (S,S) configuration, and an organic or inorganic base, to obtain the compound of formula (7a) or (7b); and deprotecting the compound of formula (7a) or (7b)

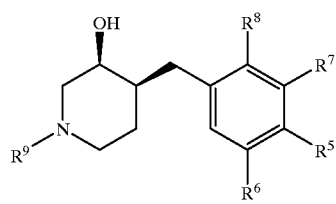
(7a)

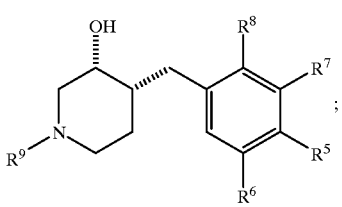
(7b)

wherein the symbols are as defined above; or
deprotecting the compound of formula (6); and
asymmetrically hydrogenating the salt of formula (6bis)

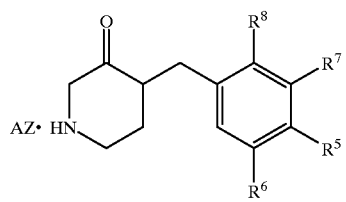
(6bis)

in presence of a ruthenium complex with a chiral diphosphine ligand and a chiral diamine, wherein the diphosphine has an (S) configuration and the diamine has an (R,R) configuration or the diphosphine has an (R) configuration and the diamine has an (S,S) configuration, and a organic or an inorganic base,
to obtain the piperidine derivative of formula III-a or III-b; and f) reacting the piperidine derivative of formula III-a or III-b

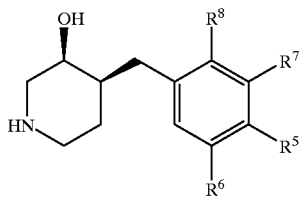
(III-a)

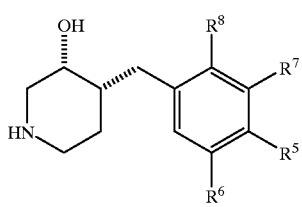
(III-b)

wherein the symbols are as defined above; with the reactive vinyl sulfone intermediate

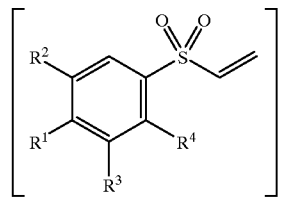
II which is obtained by treating the sulfone derivative of formula II

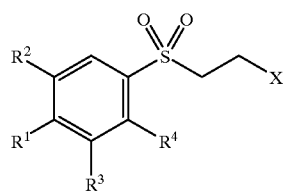
II wherein $R^1$–$R^4$ are as defined above; and

X is a leaving group; with a base;

in the presence of a base to form the desired compound of formula I-a or I-b.

2. The process of claim 1 for the preparation of compounds of formula I-a wherein in the ruthenium complex of step e), the diphosphine has an (S) configuration and the diamine has an (R,R) configuration.

3. A process for the preparation of compounds of formula

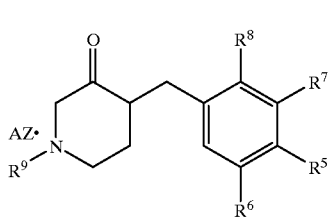
(6)

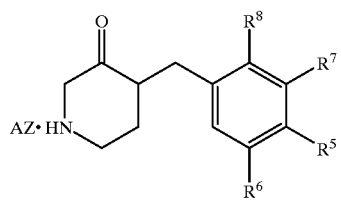
(6bis)

wherein $R^1$–$R^4$ are, independently from each other, hydrogen, halogen, hydroxy, amino, nitro, lower-alkyl-sulfonylamido, or acetamido;

$R^5$–$R^8$ are, independently from each other, hydrogen, lower-alkyl, halogen, trifluoromethyl or lower-alkoxy;

$R^9$ is an amino protecting group;

AZ signifies a mineral acid or a strong organic acid;

which process comprises
  a) reacting a protected amino acid ester (1)

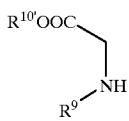

(1)

with a 4-substituted butyric acid derivative (2)

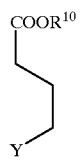

(2)

wherein
  $R^9$ is an amino protecting group, preferably benzyl;
  $R^{10}$ and $R^{10'}$ are independently a carboxylic acid protecting group; and
  Y represents a leaving group;
in the presence of a base; to obtain the protected alkoxycarbonylmethylamino butyric acid derivative (3);
  b) cyclising the protected alkoxycarbonylmethyl amino butyric acid derivative (3)

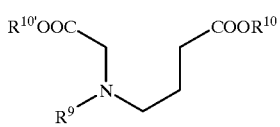

(3)

wherein the symbols are as defined above to obtain the protected alkyl-3-oxo-piperidine caboxylate salt (4);
  c) benzylating the protected alkyl 3-oxo-piperidine carboxylate salt(4)

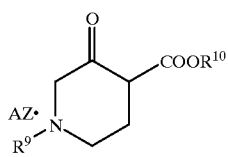

(4)

wherein
  AZ signifies a mineral acid or a strong organic acid to obtain the benzylated protected alkyl-3-oxo-piperidine carboxylate (5);
  d) decarboxylating the benzylated protected alkyl 3-oxo-piperidine carboxylate (5)

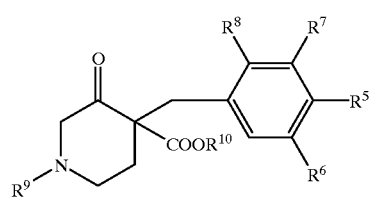

(5)

wherein the symbols are as defined above;
in presence of a strong acid to obtain the compound of formula (6);

e) deprotecting compound of formula (6) to obtain compound of formula (6bis).

4. A process for the preparation of compounds of formula

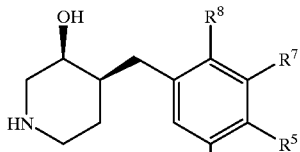

III-a and

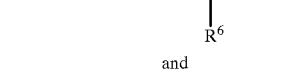

III-b wherein
  $R^1$–$R^4$ are, independently from each other, hydrogen, halogen, hydroxy, amino, nitro, lower-alkyl-sulfonylamido, or acetamido;
  $R^5$–$R^8$ are, independently from each, other hydrogen, lower-alkyl, halogen, trifluoromethyl or lower-alkoxy;
and their pharmaceutically acceptable acid addition salts, which process comprises asymmetrically hydrogenating a salt of formula (6)

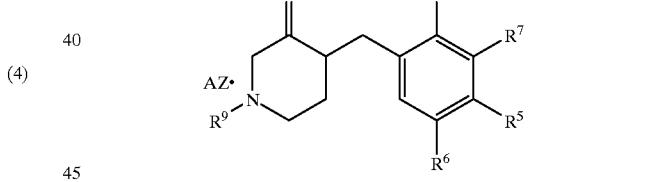

(6)

wherein $R^9$ is an amino protecting group;
in presence of a ruthenium complex with a chiral diphosphine ligand and a chiral diamine, wherein the diphosphine has an (S) configuration and the diamine has an (R,R) configuration or the diphosphine has an (R) configuration and the diamine has an (S,S) configuration, and an organic or inorganic base,
to obtain the compound of formula (7a) or (7b);
and deprotecting the compound of formula (7a) or (7b)

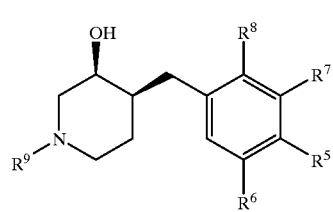

(7a)

-continued (7b)

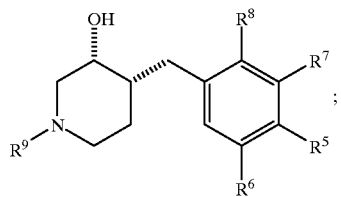

wherein the symbols are as defined above; or deprotecting the compound of formula (6); and asymmetrically hydrogenating the salt of formula (6bis)

(6 bis)

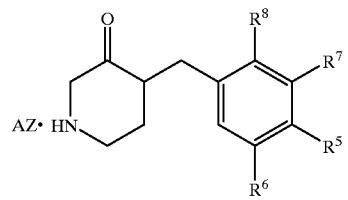

in presence of a ruthenium complex with a chiral diphosphine ligand and a chiral diamine, wherein the diphosphine has an (S) configuration and the diamine has an (R,R) configuration or the diphosphine has an (R) configuration and the diamine has an (S,S) configuration, and an organic or inorganic base, to obtain the piperidine derivative of formula III-a or III-b.

5. The process of claim 4 for the preparation of compounds of formula III-a wherein in the ruthenium complex, the diphosphine has an (S) configuration and the diamine has an (R,R) configuration.

6. A process of claim 4, wherein the asymmetric hydrogenation is characterized in that the ruthenium complex is a complex of formula Ru(E)$_2$(L)(A)    IV wherein E is a halogen atom;
L is a chiral diphosphine ligand; and
A is a chiral diamine;

the chiral diphosphine ligands are ligands of formulae

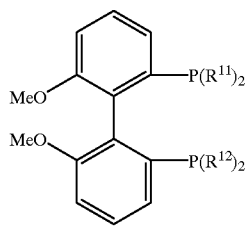 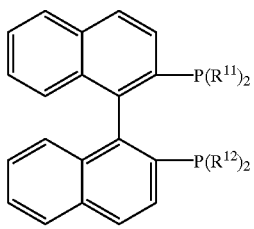

-continued

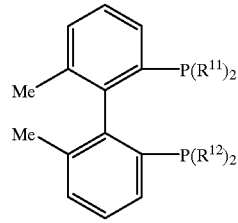

wherein

R$^{11}$ and R$^{12}$ are independently from each other alkyl, cycloalkyl, optionally substituted phenyl or a heterocyclic ring;

and the chiral diamines are compounds of formulae

V

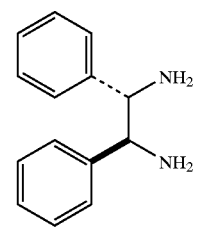

VI

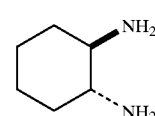

VII

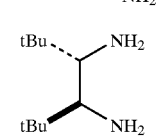

VIII

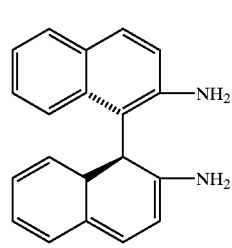

IX

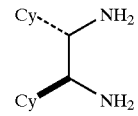

X

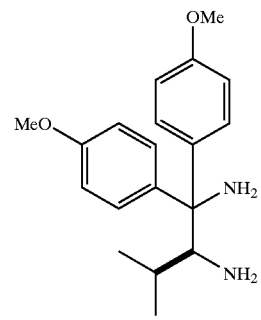

wherein tBu signifies tert.-butyl, Me is methyl and Cy stands for cyclohexane.

7. A process of claim 6, wherein $R^{11}$ and $R^{12}$ are independently from each other

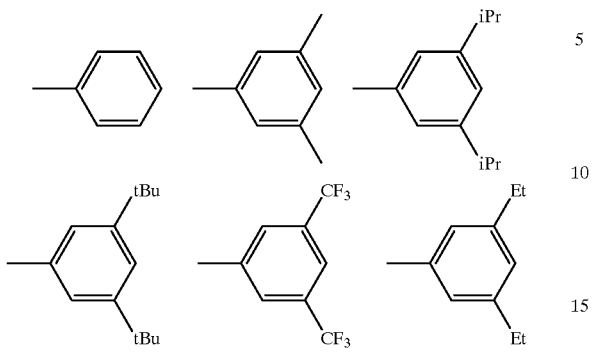

wherein iPr is iso-propyl and tBu is tert.-butyl.

8. A process of claim 7, characterized in that the chiral diamine is a compound of formula V.

9. A process of claim 5, wherein the amount of chiral diamine used in the reaction is about 0.5 to about 2.5 equivalents based on the Ru-complex.

10. A process of claim 4 wherein the organic or inorganic base is present in the amount of about 1.0 to about 0.001 mol equivalents with respect to the substrate in addition to the about 1 mol equivalent of organic or inorganic base present for the neutralization of the acid salt of the substrate (6) or (6 bis).

11. A process of claim 10 wherein the organic or inorganic base is present in the amount of about 0.05 about 0.2 mol equivalents with respect to the substrate in addition to the about 1 mol equivalent of organic or inorganic base present for the neutralization of the acid salt of the substrate (6) or (6 bis).

12. A process of claim 4 wherein the organic or inorganic base is potassium tert.-butylate.

13. A process of claim 1, for the preparation of compounds of formulae

I-a

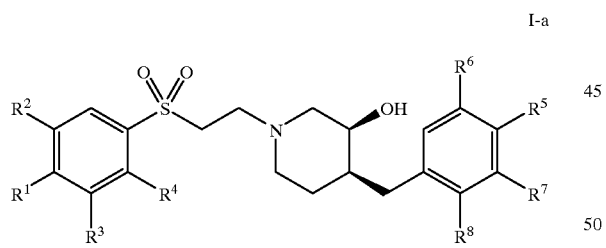

I-b

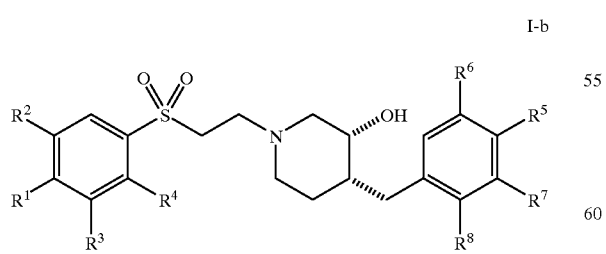

wherein
  $R^1$–$R^4$ are, independently from each other, hydrogen, halogen, hydroxy, amino, nitro, lower-alkyl-sulfonylamido, or acetamido;

$R^5$–$R^8$ are, independently from each, other hydrogen, lower-alkyl, halogen, trifluoromethyl or lower-alkoxy; and their pharmaceutically acceptable acid addition salts; which process comprises a) deprotonating a substituted thiophenol derivative of formula (8)

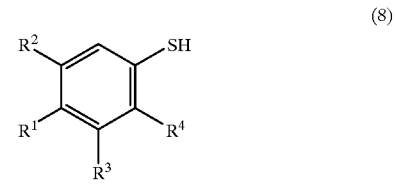

(8)

wherein the symbols are as defined above;
in presence of a strong inorganic or organic base and subsequently reacting it with 2-haloethanol to obtain the thioether of formula (9);

b) oxidizing the thioether of formula (9)

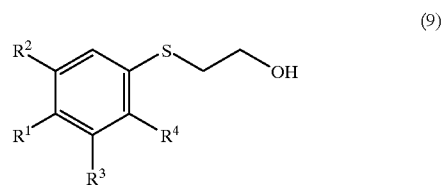

(9)

wherein the symbols are as defined above;
in presence of an oxidative agent to obtain the sulfone derivative of formula (10);

c) replacing the hydroxy group of the sulfone derivative of formula (10)

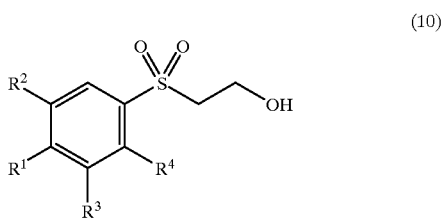

(10)

wherein the symbols are as defined above;
by a halogen atom in the presence of pyridine in dichloromethane to obtain the sulfone derivative of formula II; and d) treating the sulfone derivative of formula II

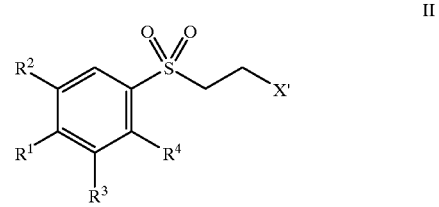

II wherein
  $R^1$–$R^4$ are as defined above; and
  X' is halogen;
with a base to form the corresponding reactive vinyl sulfone intermediate of formula II*

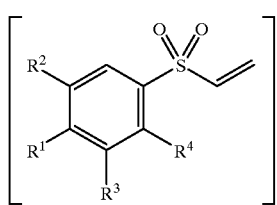

II* which is then reacted with the piperidine derivative of formula

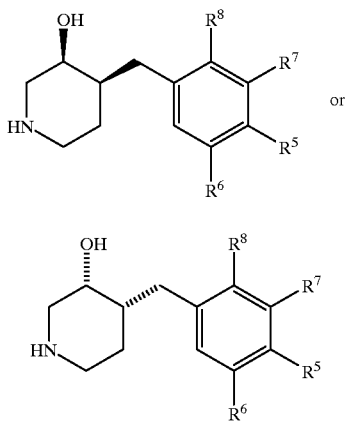

III-a or

III-b wherein the symbols are as defined above;
in presence of a base to obtain the compounds of formulae I-a or I-b.

14. A process of claim 13 for the preparation of compounds of formula

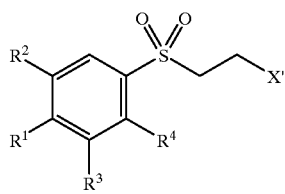

II wherein
$R^1$–$R^4$ are, independently from each other, hydrogen, halogen, hydroxy, amino, nitro, lower-alkyl-sulfonylamido, or acetamido; and
X' is halogen;
which process comprises
a) deprotonating a substituted thiophenol derivative of formula (8)

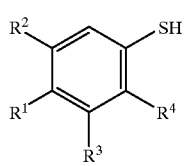

(8)

wherein the symbols are as defined above;

in presence of a strong inorganic or organic base and subsequently reacting it with 2-haloethanol to obtain the thioether of formula (9);
b) oxidizing the thioether of formula (9)

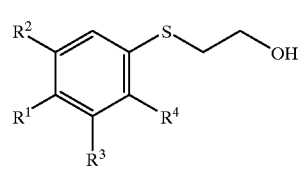

(9)

wherein the symbols are as defined above;
in presence of an oxidative agent to obtain the sulfone derivative of formula (10);
c) replacing the hydroxy group of the sulfone derivative of formula (10)

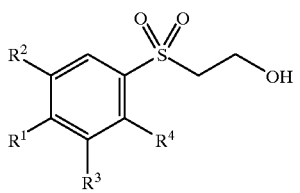

(10)

wherein the symbols are as defined above;
by a halogen atom in the presence of pyridine in dichloromethane to obtain the compound of formula II.

15. Compounds of formula (6)

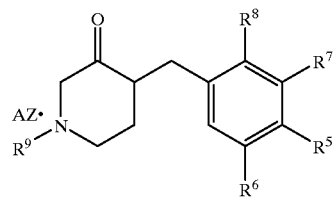

wherein $R^5$–$R^8$ are, independently from each other, hydrogen, lower-alkyl, halogen, trifluoromethyl or lower-alkoxy, BY is an amino protecting group, and AZ is a mineral acid or a strong organic acid.

16. Compounds of formula (6 bis)

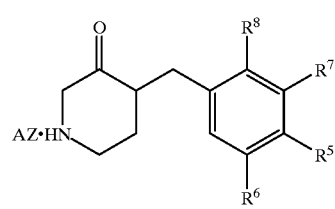

(6bis)

wherein $R^5$–$R^8$ are, independently from each other, hydrogen, lower-alkyl, halogen, trifluoromethyl or lower-alkoxy and AZ is a mineral acid or a strong organic acid.

* * * * *

UNITED STATES PATENT AND TRADEMARK OFFICE
CERTIFICATE OF CORRECTION

PATENT NO. : 6,605,723 B2
DATED : August 12, 2003
INVENTOR(S) : Crameri et al.

It is certified that error appears in the above-identified patent and that said Letters Patent is hereby corrected as shown below:

Title page, Item [54] and Column 1, lines 1-3,
Title reads "PROCESS FOR THE PREPARATION OF ETHANESUL FONYL-PIPERIDINE DERIVATIVES" should read -- PROCESS FOR THE PREPARATION OF ETHANESULFONYL-PIPERIDINE DERIVATIVES --.

Title page,
Item [73], Assignee, "Hoffman-La Roche Inc., Nutley, NJ (US)" should read -- Hoffmann-La Roche Inc., Nutley, NJ (US) --.

Column 50,
Line 48, "BY is an amino" should read -- $R^9$ is an amino --.

Signed and Sealed this

Sixth Day of January, 2004

JAMES E. ROGAN
*Director of the United States Patent and Trademark Office*